(12) United States Patent
Lynes et al.

(10) Patent No.: US 6,723,523 B2
(45) Date of Patent: Apr. 20, 2004

(54) SYSTEM AND METHOD FOR INVESTIGATING THE EFFECT OF CHEMICAL AND OTHER FACTORS ON CELL MOVEMENT

(75) Inventors: Michael A. Lynes, Willington, CT (US); David A. Knecht, Storrs, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 10/002,961

(22) Filed: Oct. 26, 2001

(65) Prior Publication Data

US 2002/0086280 A1 Jul. 4, 2002

Related U.S. Application Data

(60) Provisional application No. 60/243,450, filed on Oct. 26, 2000.

(51) Int. Cl.[7] .......................... G01N 33/567; C12N 3/00

(52) U.S. Cl. ................ 435/7.21; 435/287.1; 435/288.4; 435/288.5

(58) Field of Search .......................... 435/7.21, 287.1, 435/288.4, 288.5

(56) References Cited

U.S. PATENT DOCUMENTS 5,023,173 A 6/1991 Horwitz et al.
5,187,096 A * 2/1993 Giaever et al.

FOREIGN PATENT DOCUMENTS

WO    WO 00/07007    10/2000

OTHER PUBLICATIONS

Nelson et al. Chemical Under Agarose: A new and simple method for measuring chemotaxis and spontaneous migratioon of human polymorphonuclear leukocytes and monocytes, Journal of Immunology, vol. 115, (1975), pp. 1650–1656.*

Nelson, R. et al., Chemotaxis Under Agarose: A New and Simple Method for Measuring Chemotaxis and Spontaneous Migration of Human Polymorphonuclear Leukocytes and Monocytes; *Journal of Immunology*, vol. 115, (1975), pp. 1650–1656.

Boyden, S., The Chemotactic Effect Of Mixtures Of Antibody And Antigen On Polymorphonuclear Leucocytes; *Journal of Experimental Medicine* 115; (1962), pp. 453–466.

(List continued on next page.)

Primary Examiner—Brenda Brumback
Assistant Examiner—Randall Winston
(74) Attorney, Agent, or Firm—McCarter & English LLP

(57) ABSTRACT

As disclosed herein, the present invention is directed to a novel system for monitoring cell movement in response to chemotactic and chemokinetic factors. In this system, cells migrate in an under-agarose environment and their position is monitored using a system capable of measuring changes in impedance and other electrical parameters of the system at a target electrode lithographed onto a substrate as the cells arrive at the target. With the disclosed system, the time of arrival of cells at the target electrode is proportional to the dose of the chemoattractant species used to stimulate the cells and can be assessed by changes in resistance at the electrode. The system is readily able to distinguish between wild-type cells and mutants that are deficient in their chemotactic response. In addition, agents that interfere with chemotactic motility can be shown to lead to delayed arrival of cells at the target electrode. The multi-well configuration of the disclosed assay system allows for simultaneous automated screening of many samples for chemotactic or anti-chemotactic activity.

10 Claims, 14 Drawing Sheets

OTHER PUBLICATIONS

Dolan, R. et al., Systemic Neutrophil Intrinsic 5–Lipoxygenase Activity and CD18 Receptor Expression Linked to Reperfusion Injury; *Laryngoscope 108*, (Sep. 1998), pp. 1386–1389.

Michna, H., Induced Locomotion of Human and Murine Macrophages; *Cell Tissue Res 255*, (1989), pp. 423–429.

Keese, C. et al., Sunstrate Mechanics and Cell Spreading; *Experimental Cell Research 195*, (1991), pp. 528–532.

Ghosh, P. et al., Monitoring Electropermeabilization in the Plasma Membrane of Adherent Mammalian Cells; *Biophys. J.* 64, (1993), pp. 1602–1609.

Noiri, E. et al., Permissive Role of Nitric Oxide in Edothelin–induced Migration of Endothelial Cells; *Journal of Biol Chem 272*, (1997), pp. 1747–1762.

Thomsen, M. et al., Reassessment of Two Boyden Chamber Methods for Measuring Canine Neutrophil Migration; *Veterinary Immunology Immunopatholy 129*, (1991) pp. 197–211.

Pei, Z. et al., Effect of the pSV2–neo Plasmid on NIH 3T3 Cell Motion Detected Electrically; *Experimental Cell Research 212*, (1994), pp. 225–229.

Panek, R. et al., In Vitro Pharmacological Characterization of PD 166285, a New Nanomolar Potent and Broadly Active Protein Tyrosine Kinase Inhibitor; *The Journal of Pharmacology and Experimental Therapeutics 283*, (1997), pp. 1433–1444.

Smith, T. et al., Prostaglandin E2 Elicits a Morphological Change in Cultural Orbital Fibroblasts from Patients with Graves Opthalmopathy; *Proc Natl Acad Sci*, vol. 91, (May 1994), pp. 5094–5098.

Tiruppathi, C. et al., Electrical Method for Detection of Endothelial Cell Shape Change in Real Time; *Am JPhysio 1264*, (1993), pp. C471–478.

Wegner, C. D., et al., Intercellular Adhesion Molecule–1(ICAM–1) in the Pathogenesis of Asthma; *Science*, vol. 247, Issue 4941 (Jan. 26, 1990) Issue 4941 (Jan. 26, 1990) pp. 456–459.

Wang, H. et al., Prostaglandin $E_2$ Alters Human Orbital Fibroblast Shape Through a Mechanism Involving the Generation of Cyclic Adenosine Monophospate; *Journal of Clinical Endocrinology and Metabolism*, vol. 80, No. 12, (1995), pp. 3553–3560.

Giaever, A. K. et al., Phosphoinositide Metabolism in a Polyoma–BK–Vitrus–Transformed Pancreatic Islet Cell Line: Evidence for Constitutively Activated Phospholipace C, *Int. J. Cancer*: 53, 1992) pp. 80–86.

Giaever, I. et al., Use of Electric Fields to Monitor the Dynamical Aspect of Cell Behavior in Tissue Culture; *IEEE Transactions of Biomedical Engineering*, vol. BME–33, No. 2, (Feb. 1986) pp. 242–247.

O'Connor, E. R. et al., Electrical Resistance Method for Measuring Volume Changes in Monolayer Cultures Applied to Primary Astrocyte Cultures; *AM. J. Physiol.* 264, (1993) pp. C471–C478.

Lo, C. et al., Impedance Analysis of MDCK Cells Measured by Electric Cell–Substrate Impedance Sensing; *Biophysical Journal*, vol. 69, (Dec. 1995) pp. 2800–2807.

Kowolenko, M. et al., Measurement of Macrophage Adherence and Spreading with Weak Electric Fields; *Journal of Immunological Methods*, (1990) pp. 71–77.

Reddy, L. et al., Assessment of Rapid Morphological Changes Associated with Elevated cAMP Levels in Human Orbital Fibroblasts; *Experimental Cell Research 245*, (1998) pp. 360–367.

Cutler, J. A Simple In Vitro Method for Studies on Chemotaxis; *Society for Experimental Biology and Medicine*, 147, (1974) pp. 471–474.

Giaever, I. et al., Cell Adhesion to Substrates Containing Absorbed or Attached IgG; *National Academy of Sciences of the United States of America*, vol. 75, Issue 3, (Mar. 1978) pp. 1366–1368.

Giaever, I. et al., A Morphological Biosensor for Mamalian Cells, *Nature*, vol. 366, (Dec. 1993) pp. 591, 592.

Giaever, I. et al., Behavior of Cells at Fluid Interfaces; *National Academy of Sciences of the United States of America*, vol. 80, Issue 1, (Jan. 1983) pp. 219–222.

Giaever, I. et al., Micromation of Mammalian Cells Measured Electrically; *National Academy of Sciences of the United States of America*, vol. 88, (1991) pp. 7896–7900.

Lo, C. et al., Monitoring Motion of Confluent Cells in Tissue Culture; *Experimental Cell Research 204*, (1993) pp. 102–109.

Lo, C. et al., pH Changes in Pulsed CO2 Incubators Cause Periodic Changes in Cell Morphology; *Experimental Cell Research 213*, (1994) pp. 391–397.

Moy, A. et al., Histamine and Thrombin Modulates Endothelial Focal Adhesion Through Centripetal and Centrifugal Forces; *The Journal of Clinical Investigation*, vol. 97, No. 4, (Feb. 1996) pp. 1020–1027.

Wright, C. et al., Selective Regulation of Human Neutrophil Functions by the Cell Activation Inhibitor C1–1959; *Journal of Leukocyte Biology*, vol. 55, (Apr. 1994) pp. 443–451.

Mitra, P. et al., Electric Measurement Can Be Used to Monitor the Attachment and Spreading of Cells in Tissue Culture; *BioTechniques*, vol. 11, No. 4 (1991) pp. 504–510.

Hidi, R. et al., Formation of LTB4 by fMLP–stimulated Alveolar Macrophages Accounts for Eosinophil Migration In Vitro; *Journal of Leukocyte Biology*, vol. 51, (Apr. 1992) pp. 425–431.

Falk, W. et al., A 48–Well Micro Chemotaxis Assembly for Rapid and Accurate Measurement of Leukocyte Migration; *Journal of Immunological Methods*, (Sep. 1979) pp. 239–247.

Vollmer, K. et al., Tumor Necrosis Factor–Alpha Decreases Neutrophil Chemotaxis to N–formyl–1–methionyl–1–leucyl–1–phenylalanie; Analysis of Single Cell Movement; *Journal of Leukocyte Biology*, vol. 52, (Dec. 1992) pp. 630–636.

Wegener, J. et al, Electric Cell–Substrate Impedance Sensing (ECIS) as as Noninvasive Means to Monitor the Kinetics of Cell Spreading to Artificial Surfaces; *Experimental Cell Research 259*, 158–166 (2000).

Luong, J. et al., Monitoring Motility, Spreading, and Mortality of Adherent Insect Cells Using an Impedance Sensor; *Analytical Chemistry*, vol. 73, No. 8, (Apr. 15, 2001), pp. 1844–1848.

\* cited by examiner

PANELS A-B

D

C

PANELS C-D

PANELS A-B

PANELS C-D

SYSTEM AND METHOD FOR INVESTIGATING THE EFFECT OF CHEMICAL AND OTHER FACTORS ON CELL MOVEMENT

REFERENCE TO RELATED APPLICATIONS

This application claims benefit under Title 35, U.S.C. § 119(e), of U.S. application Ser. No. 60/243,450, filed Oct. 26, 2000.

FIELD OF THE INVENTION

The present invention relates, in general, to novel methods for measuring cell movement and to methods for assessing the impact of a variety of factors on the ability of cells to move. In particular, the present invention relates to systems and methods for measuring cell movement and the effect of various chemical species on that phenomenon by monitoring one or more electrical parameters of sensing electrodes that are sensitive to the interaction of cells with the electrode surface.

BACKGROUND OF THE INVENTION

Cells move from place to place in multicellular organisms for a variety of reasons. For example, cell movement occurs during organogenesis, movement is essential to inflammatory immune responses, and movement of neoplastic cells permits metastasis to secondary sites. This movement can arise from the intrinsic characteristics of the cell, or it can be initiated, enhanced or otherwise affected by the presence of external chemical stimuli. Stimuli can be divided into two classes: those that stimulate cell movement without a specific directional aspect (chemokinesis), and those stimuli that enhance directional cell movement according to the location of external cues (chemotaxis).

Cell movement is a critical component of both normal immune function and the dysfunctional immune responses associated with certain disease conditions such as asthma, chronic inflammation and autoimmune disease. Often this movement is characterized as chemotactic, and is initiated in response to the presence of one or more of a set of chemoattractants. These chemoattractant species (e.g., chemokines and activated components of the complement cascade) can be produced by the body in response to a variety of stimuli. Additionally, cells of the immune system are capable of rapid and vigorous responses to stimuli provided by infectious microorganisms (e.g., f-met-leu-phe and other formulated peptides that are products of bacterial protein degradation). In the context of an infection or other inflammation, these signals cause the influx of cells (notably macrophages and neutrophils) at the site of inflammation. The common mechanism of action for these signals is to engage specific receptors on the surface of the cell. Following ligand/receptor engagement, one or more signal transduction cascades are initiated, and the cell responds by specific activation of genes and the movement of the cell along the gradient. Still unknown is the means by which these cells sense the gradient, and the actual mechanisms by which they move through the cellular environment to arrive at the source of the chemoattractant.

From a practical standpoint, studies that identify new chemokines and other attractants, that characterize the signal transduction cascade and the differentiation of the responding cell, as well as studies that characterize the environment in which movement occurs, will each provide potential avenues of therapeutic manipulation. Assays that measure cellular movement in response to a chemotactic gradient offer the ability to assess individual elements along the length of the path from initiation of the response to the cellular accomplishment of the movement.

Quantitative and qualitative measurement of cell movement can be important to the characterization of biological responses, such as those mentioned above, as well as to many others. The rational design of therapeutic strategies for clinical intervention in these systems can theoretically depend upon manipulation of cellular motility: increasing it when a more robust response is desired, and diminishing the influx of cells to reduce their contributions to the response. For example, pharmacological manipulations of cell accumulation in the airways has been found to be an effective treatment for some forms of asthma, and interference with cellular movement through the vascular epithelia can diminish some the inflammatory damage associated with ischemia/reperfusion injury. Vigorous research efforts are currently underway in many biotechnology and pharmaceutical laboratories to discover novel therapeutics with the capacity to affect cell movement. For example, it is understood in the art that a potential therapeutic approach is to use inhibitors of signal transduction to manipulate chemotactic responsiveness, and many investigations are currently under way to assess the viability of such an approach in the treatment of a number of disease conditions. Essential to these investigations is the capacity to make qualitative and quantitative observations of cell movement in response to chemotactic stimuli, as well as mediation of that response by inhibitors or enhancers of chemotactic response.

In the prior art, measurement of cell movement directed by chemotactic agents has been accomplished in several ways. A "small-population" assay can optically measure the movement of cells in an initial localized deposit of these cells in a chemotactic gradient that exists in proximity to the cells. Variations of the Boyden chamber assay (Boyden, S., *Journal of Experimental Medicine* 115: 453 (1953)) are currently the most commonly used. In these assays, the cells are placed on a microporous membrane over a source of chemotactic agent. As the cells detect the higher concentrations of chemotactic agent that diffuse from the source, they migrate through the membrane to its underside. Migrating cells are usually statically detected by manual and optically aided methods on the reverse side of the membrane after staining. The quantity of responding cells is usually determined as an endpoint assay at a predetermined time-point. Thus, assays of this sort are usually capable of a semi-quantitative measure of the number of cells from an initial cell population that travel across a membrane in response to a perceived gradient of a chemoattractive agent. An advantage of this type of technique is the ability to perform many simultaneous assays, as multi-well plates in a two-dimensional array may be effectively utilized. However, a major limitation of a Boyden-type assay is that the chemical gradient sensed by the cells is very steep and dissipates rapidly. Essentially, there is a high concentration of chemoattractant on one side of the separating membrane and none on the other. In addition, it is also difficult to visualize the movement of cells through the membrane in this chemotactic environment. Finally, quantitation of the number of cells to move in response to the chemotactic stimulus is limited by traditional cell-counting methodologies and other errors inherent in the system such as the loss of migrated cells from the underside of the membrane where counting occurs.

Another technique used to measure chemotaxis is to track cell movement by video microscopy in a Zigmond or Dunn chamber. In these assays, the movement of cells is recorded as they respond to an aqueous gradient of chemoattractant formed between two closely spaced glass surfaces. This assay suffers from serous drawbacks in that it is more difficult to set up, only a small number of cells can be analyzed at one time, and the assay cannot be easily multiplexed.

The under-agarose chemotactic assay (Nelson, R. D., et al. *Journal of Immunology* 115: 1650–1656 (1975)) provides a different approach from that offered in other, Boyden-type assays. In the under-agarose assay, a planar layer of agarose gel is cast in a cell culture dish. Multiple wells are cut in the agarose layer with a device such as a stainless steel punch. In a typical assay, multiple sets of three wells are punched in a linear array. In the middle well of the three-well set, a portion of cell suspension is added to the well. In one of the adjoining wells, a solution of a chemotactic agent is added. In the third well, a suitable control solution is added. The assembly is allowed to incubate at an appropriate temperature for a pre-determined period of time after which the cells are fixed with the agarose layer in place by the addition of suitable fixing agents such as absolute methanol. After fixation, the gel layer is removed and the plates stained. The migration patterns of the cells are observed optically and measurements taken of individual cells along paths toward the chemoattractant well and compared with the movement of cells toward the control well.

This type of assay provides a significantly different type of cell environment than that utilized in a Boyden-type assay. First, the cells under investigation move while surrounded by the underlying substrate (glass culture dish) and the overlying agarose layer. Second, the chemotactic gradient is stabilized by the agarose allowing the gradient to be established over a larger volume, and for a longer period of time. As indicated above, the under-agarose assay measures the distance cells move in a specified period of time as an indication of a chemotactic response. This assay has the advantage that a single endpoint need not be evaluated since the cells gradually spread away from the starting well. The disadvantage is that in running many parallel assays, each would have to be evaluated microscopically at many time points to get an estimate of the extent of movement in each assay. Furthermore, the nature of the measurements obtained with this assay render it very difficult to quantify the rate at which cells move in response to chemotactic stimuli.

In the interest of obtaining information on a totally different type of cell motion, Giaever and Keese have developed an electrochemical-based system for assessing cell motility, as disclosed in U.S. Pat. No. 5,187,096, the disclosure of which is hereby incorporated in its entirety. A commercialization of this system, known as the Electric Cell Impedance Sensing ("ECIS") system has been developed and is sold by Applied Biophysics, Inc. (Troy, N.Y.).

In the ECIS assay system, two electrodes are lithographed onto the surface of a lexan slide and positioned within a chamber that holds aqueous media. Cells in this media can attach to a sensing electrode and to the surrounding surface of the slide. A 1 volt a.c. current passes through the culture media that functions as an electrolyte, and a lock-in amplifier measures current flow through this circuit. This measurement provides data on the initial resistance of the system and, more importantly, any changes to current flow on the electrode that occur over time. Due to the relatively small size of the electrode, resistance at the sensing electrode predominates in the system. Any activity that affects the adherence of cells to the electrodes will alter the measured electrical resistance in the system. For example, increasing the tightness of association of cells with the surface of the electrode by coating it with extracellular matrix proteins increases the resistance of the electrical circuit. Lipopolysaccharide (LPS) activates macrophages to spread and cover a larger amount of the target electrode and thus also increase the resistance measured at the target electrode. In contrast, toxicants that damage cells will act to reduce the resistance of the circuit. The degree of or changes in cell motility will also be reflected by changes in the measured electrode resistance as the extent of interaction between the cells and the electrode surface changes.

FIG. 1 illustrates a typical prior art ECIS configuration with a side view (not to scale) of cells 54 sitting on the sensing electrode 10 in a culture well 50. The electrodes comprise gold electrodes fabricated on plastic substrata 58. Culture media 55 is used as the electrolyte. In a typical ECIS application, a constant AC current of 1 microampere at 4 kHz is maintained between the sensing electrode 10 and a large counter electrode 40, while the voltage is monitored with a lock-in amplifier 52. Voltage and phase data are stored and processed with a microprocessor 60. Normally, these data are converted to resistance or capacitance by treating the cell-electrode system as a series RC circuit. The same microprocessor controls the output of the amplifier and switches the measurement to different sensing electrodes in the course of an experiment with a multi-cell array.

In an ECIS system, the relative sizes of the sensing and counter electrodes can be significant. With larger sensing electrodes, cell-related resistance signals become difficult to detect. This is a consequence of bulk solution resistances that tend to swamp out the contribution to total resistance from the sensing electrode. When electrodes have a surface area of approximately $10^{-3}$ cm$^2$ or less, the impedance of the electrode-electrolyte interface at 4 kHz predominates, and in this situation, changes in resistance due to interaction of the cells with the electrode surface are clearly revealed.

In a typical assay, cells seeded into an ECIS well settle to the bottom of the well, attach to the surface of the sensing electrode 10 that is fabricated on the bottom surface of the well, and individual cells spread radially. The number of cells on the well, the intimacy of contact, the degree of spreading, and the activity (motility) of the cells all contribute to the level of resistance imparted by the cells to the circuit. A single electrode can be monitored as often as four times per second with currently available hardware in the commercial embodiment of the ECIS system. The intimacy of cell contact with the electrode can be modified by pre-incubation of the electrode with different extracellular matrix proteins and this can result in different levels of resistance imparted by the cells to the system. Moreover, the intimacy of contact can be modified by exposing the cells to agents that alter the viability, signal transduction, or membrane integrity of the cell.

As disclosed in U.S. Pat. No. 5,187,096, cited above, the ECIS system is directed toward investigations of cellular phenomena that are only remotely implicated in the type of cell movement associated with chemotactic or chemokinetic behavior. As such, its utility, although specialized, does not extend in its conventional applications to investigations into the mechanism of translational cell movement, or the influence of chemical agents on that motion.

Consequently, there exists a need in the art for an assay system directed toward translational cell movement that is capable of rapid, automated and multiplexed analysis of cell movement and factors capable of affecting such movement. In a unique combination of the traditional under-agarose cell assay with the specific capabilities of an ECIS system, the present inventors have developed a system and methods for investigation of phenomena associated with cell movement that possesses these desirable characteristics, and addresses the majority of the shortcomings associated with prior art techniques. Specific embodiments of these systems and methods are detailed below.

SUMMARY OF THE INVENTION

In a first embodiment, the present invention provides a system for monitoring the effect of extracellular chemical stimuli on the translational motion of cells, the system comprising: (a) an array of one or more cell containment volumes; (b) an array of one or more chemical agent volumes interspersed among the array of one or more cell containment volumes; (c) one or more substantially planar sensing electrodes distributed within the arrays of cell containment volumes and chemical agent volumes so that at least one of the sensing electrodes is between one cell containment volume and one chemical agent volume, wherein the one or more sensing electrodes is operatively coupled to a sensing device capable of measuring an electrical parameter of the sensing electrode; (d) at least one counter electrode in electrical connection with the one or more sensing electrodes; and (e) a biocompatible chemical gradient stabilizing medium in simultaneous diffusional contact with the arrays of cell containment volumes and chemical agent volumes. In this embodiment of the present invention, the at least one counter electrode and the one or more sensing electrodes are connected in series.

In addition, the present invention contemplates a system wherein the at least one counter electrode and the one or more sensing electrodes are connected in parallel. Alternatively, the at least one counter electrode and the one or more sensing electrodes are connected in series. Also, the system of the invention can further comprise a reference electrode in electrical connection to the at least one counter electrode and the one or more sensing electrodes. The system of the invention also contemplates that the measured electrical parameter of the sensing electrode is impedance, or resistance, or capacitance.

As exemplified in this embodiment, the system of the invention contemplates a chemical gradient stabilizing medium that is in a planar geometry overlying the arrays of cell containment volumes and chemical agent volumes. Preferably, the chemical gradient stabilizing medium is an agarose gel. Furthermore, preferentially, the geometry of the sensing electrode is substantially circular. Alternatively, the geometry of the sensing electrode can be substantially rectangular. It is also possible that the geometry of the sensing electrode is semi-circular. Preferably, the surface area of each of the one or more sensing electrodes is from about $0.5 \times 10^{-2}$ mm$^2$ to about $10 \times 10^{-2}$ mm$^2$.

In a particularly preferred embodiment, the system of the present invention comprises a sensing device that is operatively coupled to a microprocessor. This microprocessor can be connected to an output display device capable of displaying the electrical parameter values measured at the one or more sensing electrodes. Preferably, the output display device is a cathode ray tube (CRT), or alternatively, a hard copy device such as plotter or printer. More preferably, the microprocessor is under the control of a software program executable on the microprocessor.

In yet another embodiment, the present invention provides a method for monitoring the translational motion of cells in response to extracellular chemical stimuli, the method comprising the steps of (a) placing a population of one or more cells in a biocompatible medium into a cell containment volume; (b) placing a chemical agent in a biocompatible medium into a chemical agent volume in diffusional contact with a biocompatible chemical gradient stabilizing medium; and (c) monitoring changes in an electrical parameter of one or more substantially planar sensing electrodes interposed between the cell containment volume and the chemical agent volume and in electrical connection with a counter electrode, wherein the changes in electrical parameter of the one or more sensing electrodes arise substantially from contact of one or more cells from the cell population with a surface of one or more of the sensing electrodes, and wherein the one or more cells have diffused to the surface of one or more of the sensing electrodes from the cell containment volume under the influence of a chemical gradient of the chemical agent in the chemical gradient stabilizing medium.

According to the present embodiment of the claimed invention, the measured electrical parameter is impedance. Alternatively, the measured electrical parameter is resistance or capacitance. In another aspect of this embodiment, the translational movement of the one or more cells is directionally focused. Alternatively, the translational movement of the one or more cells is not directionally focused. In yet another aspect of this embodiment, there is additionally interposed between the cell containment volume and the one or more sensing electrodes one or more barriers to translational motion of the cells. The present invention contemplates that the barrier is physical in nature. Alternatively, the barrier may be chemical in nature. In an alternative configuration of this embodiment of the claimed invention, the sensing electrode and the counter electrode are in electrical connection with a reference electrode.

In the practice of the present invention, the one or more cells are exposed to two or more independent chemical gradients from different chemical agents. In this aspect, the independent chemical gradients are physically overlapping. Alternatively, the independent chemical gradients are not physically overlapping.

According to this embodiment of the present invention, the cells of the cell population are selected from the group consisting of *D. discoideum*, bone marrow cells from BALB/c mice, M1 cells, U937 cells, and other motile eukaryotic cells from both tissue culture and from living animals.

In addition, in the practice of the claimed invention, the chemical agent may be selected from the group consisting of folic acid, guinea pig serum, activated complement, bacterial peptides, and mammalian chemokines.

The present embodiment also contemplates that the chemical agent volume is the biocompatible chemical gradient stabilizing medium.

In still another embodiment, the claimed invention provides a method for determining the impact of a test substance on the ability of a chemical agent to affect the translational movement of cells, the method comprising the steps of (a) placing a population of one or more cells in a biocompatible medium into a cell containment volume; (b) placing a chemical agent in a biocompatible medium into a chemical agent volume in diffusional contact with a biocompatible chemical gradient stabilizing medium; (c) exposing one or more cells of the population to a test substance; (d) monitoring one or more electrical parameters measured on a substantially planar sensing electrode positioned between the cell containment volume and the chemical agent volume, wherein the changes in impedance on the sensing electrode arise substantially from contact of one or more cells from the cell population with a surface of the sensing electrode, and wherein the one or more cells have diffused to the surface of the sensing electrode from the cell containment volume under the influence of a chemical gradient of the chemical agent in the chemical gradient stabilizing medium between the cell containment volume and the chemical agent volume; and (e) comparing the one or more electrical parameters measured in step (d) with electrical parameter measurements taken for one or more cells from the population that have not been exposed to the test substance.

As practiced, the method of the present invention contemplates that the measured electrical parameter is impedance. Alternatively, the measured electrical parameter is resistance or capacitance.

In addition, the method of the claimed invention further contemplates exposing the cells to a second test substance and comparing the resulting measured electrical parameter readings with corresponding electrical measurements taken for one or more cells from the population that have been exposed to the first test substance but not the second test substance.

In one aspect of this embodiment of the claimed invention, the translational movement of the one or more cells is directionally focused. Alternatively, the translational movement of the one or more cells is not directionally focused. In yet another aspect, there is additionally interposed between the cell containment volume and the one or more sensing electrodes one or more barriers to translational motion of the cells. The one or more barriers may be physical in nature and/or chemical in nature.

In an alternative embodiment, the present invention provides a system for the non-optical imaging of translational cell movement comprising (a) one or more cell containment volumes; (b) one or more chemical agent volumes; (c) a plurality of sensing electrodes interposed between the cell containment volumes and the chemical agent volumes, wherein each of the plurality of sensing electrodes is operatively coupled to a sensing device capable of measuring an electrical parameter of the sensing electrode; (d) at least one counter electrode in electrical connection with the array of sensing electrodes; and (e) a biocompatible chemical gradient stabilizing medium in simultaneous diffusional contact with the cell containment volumes and the chemical agent volumes. Preferably, the plurality of sensing electrodes are arranged in an orderly, two-dimensional array. In this embodiment, the dimensions of individual sensing electrodes is of an order that is not much larger than the dimensions of a typical cell such that the electrode surface is large enough to hold only one cell at a time. As configured, this embodiment of the invention comprises an array of at least 100 sensing electrodes. Preferably, the array comprises at least 1000 sensing electrodes. More preferably, at least 2500 sensing electrodes.

In this embodiment the electrical parameter measured at the sensing electrode is impedance. Alternatively, the electrical parameter is resistance or capacitance. This embodiment of the invention also contemplates the further inclusion of a reference electrode in electrical connection to the at least one counter electrode and the array of sensing electrodes. In addition, the present invention provides that the chemical gradient stabilizing medium is in a planar geometry overlying the arrays of cell containment volumes and chemical agent volumes. Preferably, the chemical gradient stabilizing medium is an agarose gel.

In a particularly preferred embodiment, the system of the present invention comprises a sensing device that is operatively coupled to a microprocessor. This microprocessor can be connected to an output display device capable of displaying the electrical parameter values measured at the one or more sensing electrodes. Preferably, the output display device is a cathode ray tube (CRT), or alternatively, a hard copy device such as plotter or printer. More preferably, the microprocessor is under the control of a software program executable on the microprocessor.

DETAILED DESCRIPTION OF THE INVENTION

Figure 1:
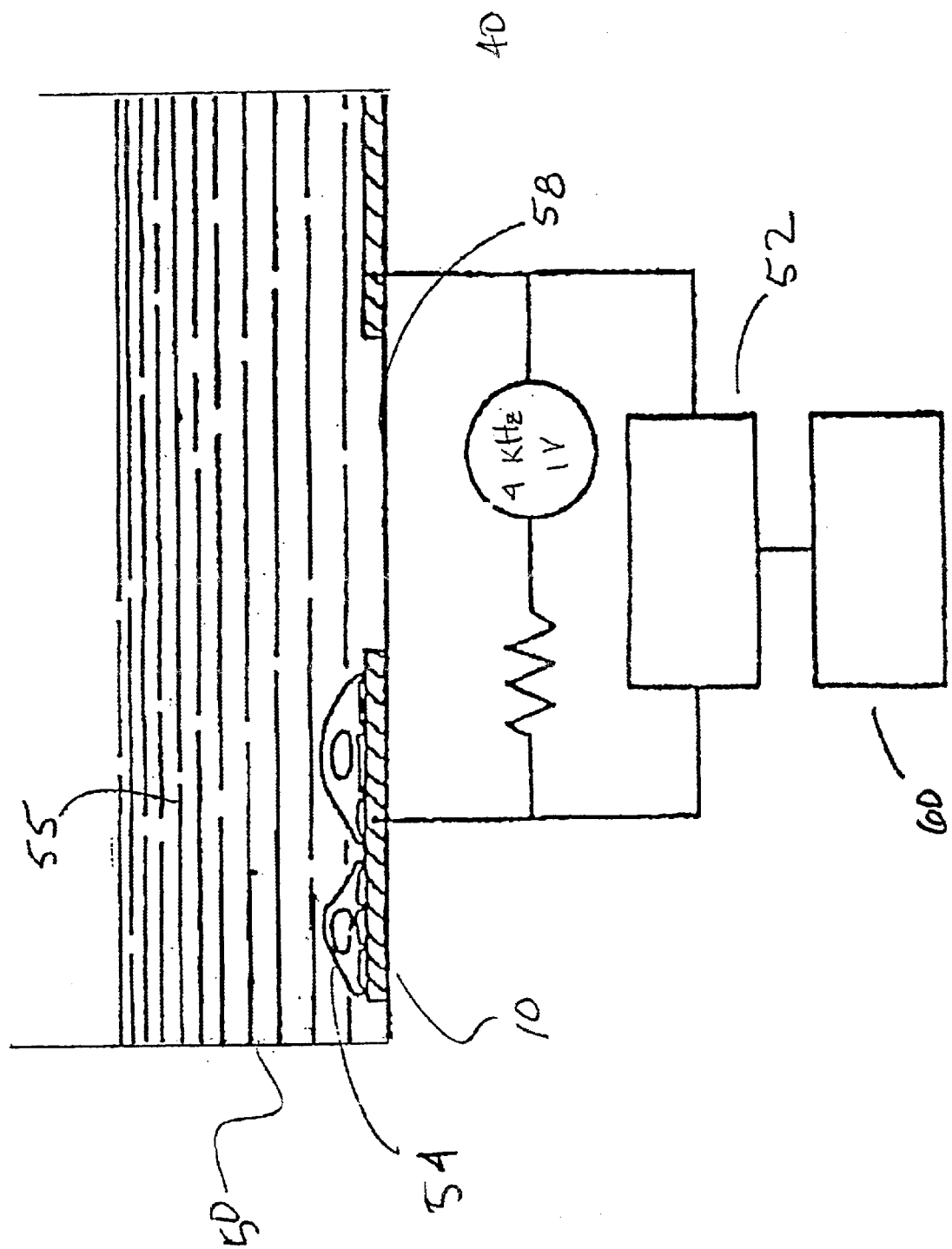
FIG. 1 is a schematic representation of a prior art ECIS system for the electrical measurement of certain types of cell activity indicative of cell motility.

In a first embodiment, the present invention provides a system for monitoring the effect of extracellular chemical stimuli on the translational motion of cells, the system comprising: (a) an array of one or more cell containment volumes; (b) an array of one or more chemical agent volumes interspersed among the array of one or more cell containment volumes; (c) one or more substantially planar sensing electrodes distributed within the arrays of cell containment volumes and chemical agent volumes so that at least one of the sensing electrodes is between one cell containment volume and one chemical agent volume, wherein the one or more sensing electrodes is operatively coupled to a sensing device capable of measuring an electrical parameter of the sensing electrode; (d) at least one counter electrode in electrical connection with the one or more sensing electrodes; and (e) a biocompatible chemical gradient stabilizing medium in simultaneous diffusional contact with the arrays of cell containment volumes and chemical agent volumes. In this embodiment of the present invention, as illustrated in panel A of FIG. 1, the at least one counter electrodes 40 and the one or more sensing electrodes 10 are connected in series although, alternatively, the present invention contemplates a system wherein the at least one counter electrode and the one or more sensing electrodes are connected in parallel. Also, the system of the invention can further comprise a reference electrode in electrical connection to the at least one counter electrode and the one or more sensing electrodes. The system of the invention also contemplates that the measured electrical parameter of the sensing electrode is impedance, or resistance, or capacitance.

In contrast to the present invention, prior art studies of cell motility are usually conducted in a laboratory by observing cells crawling on a glass coverslip in liquid media. Under these conditions, there is little to resist the movement of the cells except their own adhesion to the substrate. However, cells in natural environments, such as amoebae moving in the soil or neutrophils extravasating through the endothelium of a capillary, are presumed to move under more restrictive conditions. In addition, movement in three-dimensional environments has the added complexity that cells do not have a clearly defined dorsal and ventral surface since they can interact with the substrate on all sides. The molecular mechanisms underlying motility in three-dimensional environments are as yet poorly defined.

Using the system of the present invention, it is possible to establish a stable chemotactic gradient in which cell responses can be measured in real time. The present system is sufficiently sensitive to detect the arrival of a single cell at the surface of the sensing electrode. Moreover, the time of arrival of migrating cells at the target electrode is relatively uniform, and enables the identification of a wave-like behavior in the movement of these cells. The Examples presented below demonstrate that the system of the present invention can be used to characterize chemoattractants, soluble antagonists of chemotaxis or novel mutants affecting chemotaxis.

The claimed system of the present invention builds upon a standard configuration of the ECIS system of Giaever and Keese to provide unique capabilities that facilitate the automated monitoring of cell population movement over time. To begin with, the system of the present invention provides a chemical gradient stabilizing medium in the form of an agarose layer 64 that covers and is in diffusional contact with the individual wells of a typical multi-chamber sample system as illustrated in Panel C of FIG. 2. This enables the establishment of a chemotactic gradient between the one or more chemical agent volumes 66 loaded with chemoattractant and the cell containment volumes 68 in which cells are initially loaded.

The agarose layer 64 that serves as the chemical gradient stabilizing medium permits the establishment of the necessary chemical gradient as chemoattractant species begin to diffuse out of the chemical agent volumes 66. Due to the unique, art-recognized physical and chemical properties of a medium such as agarose, the resulting chemical gradient that is sensed by the cells in the cell containment volume comprises a greater volume and persists for a much longer time than the type of gradient that exists in the prior art Boyden-type chemotactic assay. As will be appreciated by one of skill in the art, alternative materials for selection of the gradient stabilizing medium are readily available. Such materials must be biocompatible with the cellular species under investigation; must provide a solution-like environment in which likely chemoattractant species are soluble; and must possess the necessary physical properties to enable controlled diffusion of soluble species through the medium. One of skill in the art, without undue experimentation, would be fully able to select alternative materials on the basis of such criteria.

The cells loaded into the one or more cell containment volumes begin to move under the influence of the gradient established by diffusion of the chemoattractant species over the substrate 58 and under the agarose layer 64 in the direction of the gradient and interact with the one or more sensing electrodes 10 in their path. The cells eventually reach and move across the sensing electrode 10 located, in a preferred embodiment, between the cell containment volume 68 and the chemical agent volumes 66, as illustrated in panel B of FIG. 2. In one embodiment, the dimensions of the sensing electrode are considerably greater than that of typical cells of interest, whose diameters, on average, would be on the order of 10 $\mu$m ($1\times10^{-5}$ m). By monitoring the changes in electrical parameters on the sensing electrode that occur over time and the occurrence of the resulting rapid transient fluctuations in resistance, for example, the arrival of cells at the electrode can be noted and measured.

Figure 2:
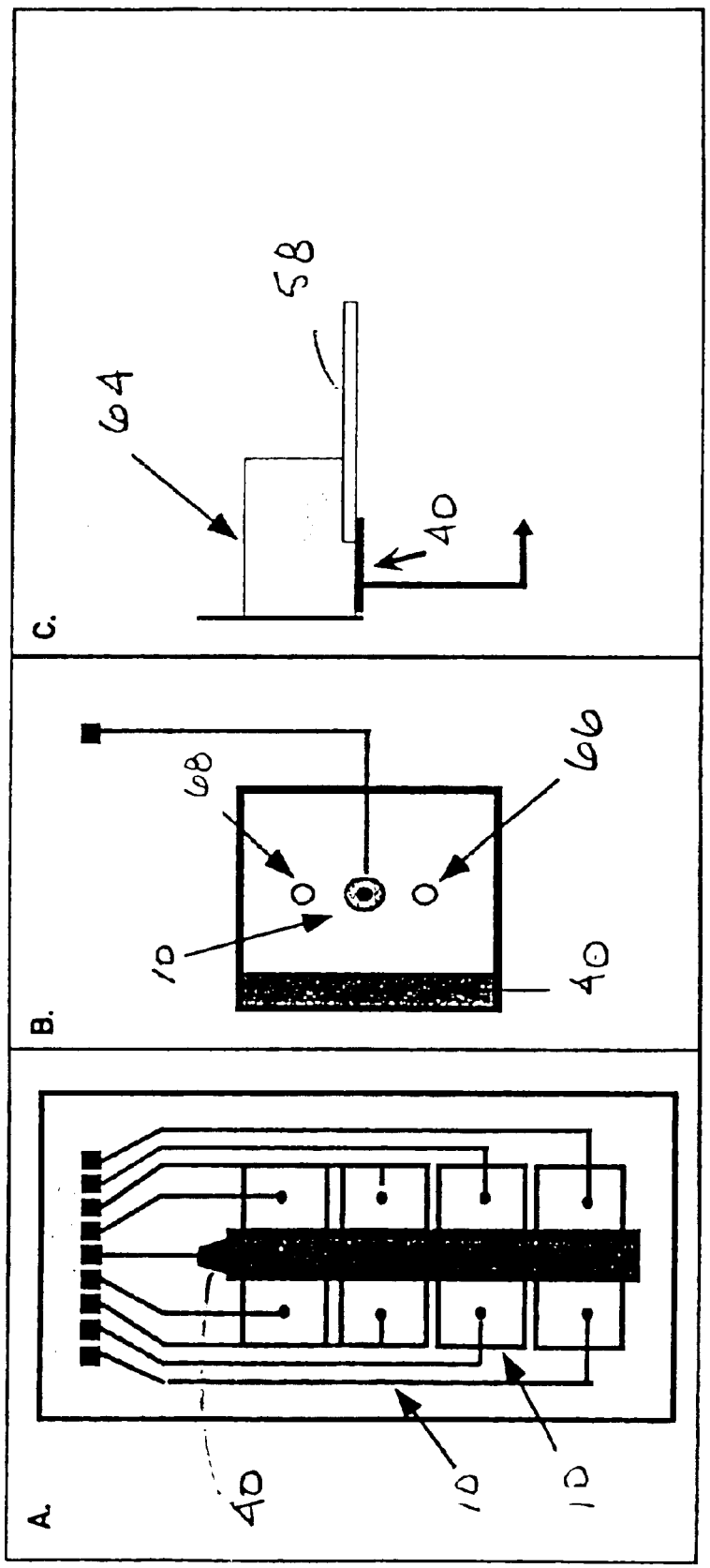
FIG. 2, in three panels, A–C, provides a schematic representation, in three views, of the cell movement assay system of the present invention.
Figure 3:
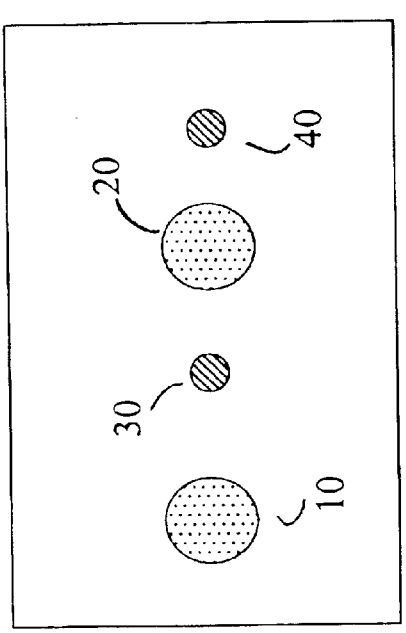
FIG. 3, in panels A–D, is an illustration of alternative electrode geometries for the cell movement assay system of the present invention.
Figure 3:
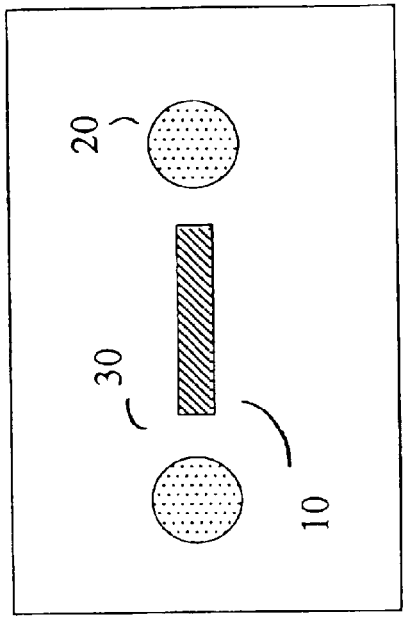
Figure 3:
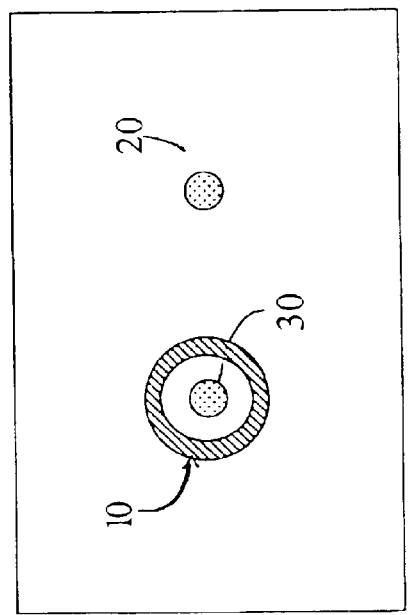
Figure 3:
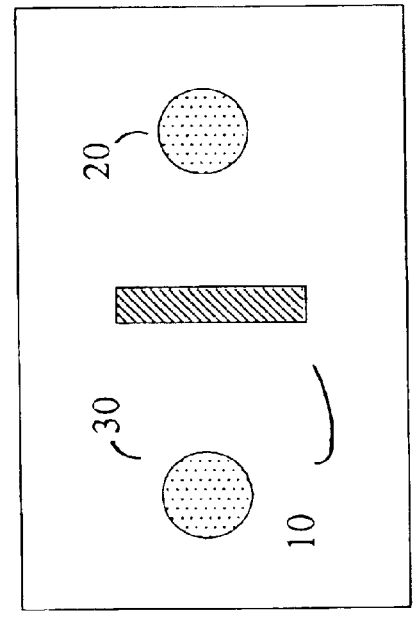

Preferably, as is illustrated schematically in FIG. 2, the geometry of the sensing electrode 10 is substantially circular. More preferably, the surface area of each of the one or more sensing electrodes is from about $0.5\times10^{-2}$ mm$^2$ to about $10\times10^{-2}$ mm$^2$. However, the practice of the present invention is not constrained to a circular geometry for the one or more sensing electrodes. As illustrated in FIG. 3, panels A–D, the sensing electrode 10, as well as the cell containment 30 and chemical agent volumes 20, can assume a number of alternative geometries. In addition, a negative chemotactic agent can be placed in a second well 40 to allow the simultaneous investigation of the effect of two different agents on cell movement. The geometry of the sensing electrode can also be substantially rectangular, as illustrated in Panels C and D of FIG. 3. It is also possible that the geometry of the sensing electrode is semicircular.

It will be appreciated that as the geometry of the sensing electrode varies, the nature of the electrical response measured at the sensing electrode may vary as well. As has been mentioned above, the movement of cells from a cell containment volume of the present system under the driving force of the chemical gradient of chemoattractant species can be detected as a psuedo-wavefront. However, the geometries of the cell containment volumes and the chemical agent volumes may also influence the nature of the cell front that reaches and is measured on the sensing electrode surface. Assuming as a first principle that the dimensions of the cell containment and chemical agent volumes are significantly smaller than the respective distances separating them from the one or more sensing electrodes, it is possible to treat the cell containment volumes and the chemical agent volumes as point sources for the species that diffuse from them. Thus, as would be expected for a diffusional point source, the expanding gradient of chemoattractant diffusing through the agarose layer would present a circular front of chemical species. For the cells moving across the substrate, it can be assumed that, in the absence of a motive force such as a gradient of chemoattractant species, the movement of cells would be non-directional in nature and would, over time, present a circular or curved front as if from a point source. Deviations in the geometry of the containment volumes would be expected to alter the nature of both the chemical gradient through the agarose, as well as potentially the nature of the front of the moving cells. Of course, under the influence of a chemoattractant species, even from a small, circular source, the movement of cells would not be expected to assume the type of form associated with random, diffusional movement. Deviations from the expected or observed characteristics of the moving front of cells may be capable of providing additional insight into the mechanisms of both cell movement and cellular response to chemotactic agents, as well as to the effects of synthetic and natural agents that alter chemotactic and chemokinetic response.

In a particularly preferred embodiment, the system of the present invention comprises a sensing device that is operatively coupled to a microprocessor. The interfacing of a microprocessor driven apparatus to the system of the present invention can greatly facilitate the collection, transformation, analysis and display of data from the sensing electrodes. Such a microprocessor can be connected to an output display device capable of displaying the electrical parameter values measured at the one or more sensing electrodes. Preferably, the output display device is a cathode ray tube (CRT), or alternatively, a hard copy device such as plotter or printer. More preferably, the microprocessor is under the control of a software program executable on the microprocessor. Commands executed on the microprocessor by the software are used to quantify the time of arrival of cells at the sensing electrode according to: (a) the development of a significant increase in the normalized resistance and (b) the development of the resistance fluctuations that are indicative of a cellular presence on the electrode. Software can be used to automatically calculate a speed of response for the cell population according to the time that cells first arrive on the small electrode. Software will also be able to make comparisons between cells operating under the sole influence of chemoattractant with cells that are exposed to chemoattractant in the presence of inhibitors of cell movement.

In yet another embodiment, the present invention provides a method for monitoring the translational motion of cells in response to extracellular chemical stimuli, the method comprising the steps of (a) placing a population of one or more cells in a biocompatible medium into a cell containment volume; (b) placing a chemical agent in a biocompatible medium into a chemical agent volume in diffusional contact with a biocompatible chemical gradient stabilizing medium; and (c) monitoring changes in an electrical parameter of one or more substantially planar sensing electrodes interposed between the cell containment volume and the chemical agent volume and in electrical connection with a counter electrode, wherein the changes in electrical parameter of the one or more sensing electrodes arise substantially from contact of one or more cells from the cell population with a surface of one or more of the sensing electrodes, and wherein the one or more cells have diffused to the surface of one or more of the sensing electrodes from the cell containment volume under the influence of a chemical gradient of the chemical agent in the chemical gradient stabilizing medium.

The present system may be used for numerous pharmacological assays as would be readily apparent to one of ordinary skill in the art. For example the system can be used to measure cell responses to chemoattractants in the presence of pharmacological inhibitors of cell movement and to assess the impact of exposure to free radicals on the ability of cells to move (sites of infection, inflammation, and neoplastic disease often have high levels of reactive oxygen species that may influence cell movement).

In the practice of the present invention, the one or more cells can be exposed to two or more independent chemical gradients from different chemical agents. In this aspect, the independent chemical gradients are physically overlapping. Alternatively, the independent chemical gradients are not physically overlapping. According to this embodiment of the present invention, the cells of the cell population are selected from the group consisting of *D. discoideum*, bone marrow cells from BALB/c mice, M1 cells, U937 cells, and other motile eukaryotic cells from both tissue culture and from living animals.

In addition, in the practice of the claimed invention, the chemical agent may be selected from the group consisting of folic acid, guinea pig serum, activated complement, bacterial peptides, and mammalian chemokines.

In an alternative embodiment, the present embodiment contemplates that the chemical agent volume is the biocompatible chemical gradient stabilizing medium. Thus, a known or suspected chemoattractant can be distributed uniformly throughout the chemical gradient stabilizing medium by methods well known to those of skill in the art. As a result, the cells in the cell containment volume do not sense a spreading diffusional front of chemoattractant species. Instead, the cells are confronted initially by a uniform chemical gradient that extends infinitely from the perspective of the cells. If the interaction of the cells with the chemoattractant species results in a chemical transformation of that species or a consumption of the species, the action of the cells will begin to create a depletion zone around the cells. This cell-initiated gradient then provides a further motive force for additional movement of the cells in the direction of the expanding gradient, providing a unique perspective on the factors influencing chemotactic cell movement.

Thus, in still another embodiment, the claimed invention provides a method for determining the impact of a test substance on the ability of a chemical agent to affect the translational movement of cells, the method comprising the steps of (a) placing a population of one or more cells in a biocompatible medium into a cell containment volume; (b) placing a chemical agent in a biocompatible medium into a chemical agent volume in diffusional contact with a biocompatible chemical gradient stabilizing medium; (c) exposing one or more cells of the population to a test substance; (d) monitoring one or more electrical parameters measured on a substantially planar sensing electrode positioned between the cell containment volume and the chemical agent volume, wherein the changes in impedance on the sensing electrode arise substantially from contact of one or more cells from the cell population with a surface of the sensing electrode, and wherein the one or more cells have diffused to the surface of the sensing electrode from the cell containment volume under the influence of a chemical gradient of the chemical agent in the chemical gradient stabilizing medium between the cell containment volume and the chemical agent volume; and (e) comparing the one or more electrical parameters measured in step (d) with electrical parameter measurements taken for one or more cells from the population that have not been exposed to the test substance. In addition, the method of the claimed invention further contemplates exposing the cells to a second test substance and comparing the resulting measured electrical parameter readings with corresponding electrical measurements taken for one or more cells from the population that have been exposed to the first test substance but not the second test substance.

The analysis of cell movement in the presence of chemotactic and chemokinetic stimuli is relevant to many different lines of basic and applied research. One of the potential beneficial utilities of the system and method of the present invention is for the study of normal immune processes, as well as for the study of disease processes including chronic inflammation, autoimmune disease, and cancer. Because the system and method of the present invention can utilize computerized assessment of experimental results according to an objective algorithm, and is also amenable to robotic set up and data capture, it will provide additional utility in many pharmaceutical and biotechnology applications, including the evaluation of anti-inflammatory drugs and in the clinical evaluation of patient immune function. The practice of the present invention also contemplates assessment of the movement of neoplastic cells and drugs that alter that form of cellular movement and, thus, provides unique assays of substances of potential therapeutic utility in the treatment of cancer. In addition, the design of the system of the present invention is amenable to a scaling up of the system to include larger numbers of chambers that will allow high throughput screening of mutant cells that have alterations in their chemotactic response, enabling the rapid identification of genes involved in regulation of cellular movement.

In one aspect of this embodiment of the claimed invention, the translational movement of the one or more cells is directionally focused (chemotactic). Alternatively, the translational movement of the one or more cells is not directionally focused (chemokinetic). In the latter instance, such movement is typically associated with the impact of "scatter agents" on cell movement that have been implicated in essential cellular functions associated with a cancerous disease state. Thus, the practice of the present invention is adaptable to investigations of non-directional cell movement associated with tumor growth and metastasis.

In yet another aspect, there is additionally interposed between the cell containment volume and the one or more sensing electrodes one or more barriers to translational motion of the cells. The one or more barriers may be physical in nature and/or chemical in nature. By observation of the interaction of cells with these barriers and the impact of this interaction on the movement of cells, it is possible to elucidate additional information on the mechanism of cell movement.

In an alternative embodiment, the present invention provides a system for the non-optical imaging of translational cell movement comprising (a) one or more cell containment volumes; (b) one or more chemical agent volumes; (c) a plurality of sensing electrodes interposed between the cell containment volumes and the chemical agent volumes, wherein each of the plurality of sensing electrodes is operatively coupled to a sensing device capable of measuring an electrical parameter of the sensing electrode; (d) at least one counter electrode in electrical connection with the array of sensing electrodes; and (e) a biocompatible chemical gradient stabilizing medium in simultaneous diffusional contact with the cell containment volumes and the chemical agent volumes. Preferably, the plurality of sensing electrodes are arranged in an orderly, two-dimensional array. In this embodiment, the dimensions of individual sensing electrodes is of an order that is not much larger than the dimensions of a typical cell such that the electrode surface is large enough to hold only one cell at a time. As configured, this embodiment of the invention comprises an array of at least 100 sensing electrodes. Preferably, the array comprises at least 1000 sensing electrodes. More preferably, at least 2500 sensing electrodes.

As discussed above, the system of the present invention is capable of displaying sufficient sensitivity to be able to respond to the interaction of a single cell with a sensing electrode. This is true even for electrodes with surface areas significantly larger than typical cells of interest. However, as also mentioned above, the system of the present invention is capable of a significant scaling up as represented by the simultaneous monitoring of a large number of sensing electrodes interacting with cells from one or more cell containment volumes. Although this scaling up contemplates the use of typical sized sensing electrodes, it is also possible to utilize a two-dimensional array of microelectrodes that can provide a unique, non-optical picture of the movement of cells in response to various stimuli. In this manner, the array of microelectrodes functions analogously to an array of pixels on a CRT screen driven by a signal from a microprocessor. Instead of emitting light of varying wavelengths in response to this signal, the microelectrode "pixels" of this embodiment of the present invention provide an electrical signal that is responsive to the interaction of individual cells with the electrode surface. By coupling this system to the control of a microprocessor and computer software executable on such microprocessor, it is possible to create a "picture" of electrical signals generated from the array of microelectrodes that can be displayed as an "image" of the motion of individual cells in the system. This provides significant advantages in terms of sensitivity and in terms of monitoring the complex factors controlling or affecting the movement of individual cells.

In certain of the examples provided below, *Dictyostelium discoideum* cells have been used to study eukaryotic cell chemotactic movement. *Dictyostelium discoideum* is an eukaryotic amoeba, which normally inhabits the soil. During its life cycle, the haploid cells undergo two distinct types of chemotactic movement. In the vegetative phase, the amoebae are attracted to folic acid, which is released by their bacterial food source, and detected by cell surface folate receptors. As the bacterial food source is depleted, *D. discoideum* enters the developmental stage of its life cycle. The number of folate receptors decreases during the first 7–9 hours of development and the cells become responsive to cAMP released by other amoebae. The number of cAMP receptors (cAR's) begins to increase immediately after the initiation of starvation and cAR1 is maximally expressed on the surface 3–4 hours into development.

The cells of *D. discoideum* thrive at ambient conditions and their mechanisms of motility are analogous to leukocytes. In moving across a substrate, these cells extend pseudopodia at their leading edge that attach to the substrate and orient the cell in the direction of travel. Dicryostelium are known to be chemotactic to a variety of agents. For example, folic acid produced by bacteria establishes a gradient that allows vegetative Dictyostelium cells to find their bacterial prey. Cyclic AMP (cAMP), a chemotactic signal produced by Dictyostelium, is used during development to direct the aggregation of individual cells to form the multicellular organism.

EXAMPLES

Example 1

Methods and Materials

Cells

*Dictyostelium discoidium* strain NC4A2 is an axenic cell line derived from the wild type NC4 line. The myosin II heavy chain mutant (HK323) was generated by homologous recombination to delete the coding portion of the gene in the NC4A2 cell line. Cells were maintained in HL5 media in 100 mm petri dishes with media changes every three days. Cells to be used for experimental procedures were harvested at mid-log phase. Cells were centrifuged at 200×g for 5 minutes at room temperature, re-suspended in fresh media and counted with a Z2 particle counter (Coulter, Miami, Fla.). Chambers were loaded with $10^6$ cells per well.

Agarose Preparation

Chemotaxis assays were adapted from the under-agarose chemotaxis method. Briefly, a 0.5% solution of GTG agarose (FMC Corporation, Rockland, Me.) was prepared in 1×SM media (10 g Difco Bacto-Peptone, 10 g glucose, 1 g yeast extract, 1.9 g $KH_2PO_4$, 0.6 g $K_2HPO_4$, 0.43 g $MgSO_4$ per liter, pH 6.5). For chemokinetic assays, 2×SM agarose media was premixed with an equal volume of 2× folic acid and then added to the chamber to harden.

Under Agarose Chemotaxis Assay

In order to prepare plates for the under agarose assay, SeaKem GTG agarose (FMC BioProducts, Rockland, Me.) was melted at concentrations as indicated in SM medium (10 g Difco Bacto-Peptone, 10 g glucose, 1 g yeast extract, 1.9 g KH2 PO4 , 0.6 g K2 HPO4, and 0.43 g MgSO4 to 1 L pH6.5) (23). Similar results were obtained with other types of agarose (ultraPURE LMP (BRL), NuSieve GTG (FMC, Inc), Ultra Low Gelling (FisherBiotech), and ultraPure (Gibco BRL)). Motility was generally higher when SM was used to prepare the agarose instead of HL-5. The agarose mixture was prepared fresh each day by mixing sterile SM (previously autoclaved) with the agarose powder and autoclaving for 5 minutes, slow exhausting and then plating as soon as possible. Four mL of agarose solution was added to each 60-mm plastic petri dish and allowed to harden for 1 hour.

Reagents

The chemoattractant folic acid (Research Organics, Inc. Cleveland, Ohio) stock at 100 mM was prepared by dissolving 0.44 g folate in 220 ul of 10 M NaOH. The final volume was adjusted to 10 ml with distilled water. The solution was filter sterilized through a 0.2 micron filter, aliquoted and stored frozen at −20° C. in the dark. The folate solution was adjusted to the appropriate concentration and added to wells one hour prior to the addition of cells to allow for establishment of the chemotactic gradient. Cisplatin (Sigma Chemical Co., St Louis, Mo.) was dissolved in phosphate buffered saline (PBS; NaCl 8 g, KCl 0.2 g, $KH_2PO_4$ 0.2 g $Na_2HPO_4$ 1.15 g in 1000 ml distilled $H_2O$) and cells were incubated with three different concentrations of cisplatin in PDF (20 mM KCl, 5 mM $MgCl_2$, $6H_2O$, 20 mM$KPO_4$, 0.5% dihydrostreptomycin sulfate, pH 6.4) for one hour. Following this incubation, the cells were washed three times in PDF and then re-suspended in PDF before placement in the cell wells of ECIS/taxis chambers.

Analysis System

The commercially available ECIS electrode configuration (Applied Biophysics, Inc., Troy, N.Y.) consists of 8 chambers per array, each with a large electrode and a small target electrode (see panel A of FIG. 2). These chambers were filled with 300 µL of a 0.5% solution of melted agarose prepared as described above. The thickness of the agarose layer is 4 mm. After the agarose had solidified, a sharpened 14 gauge cannula (Becton Dickinson, Rutherford, N.J.) was used to punch wells at appropriate locations in the agarose. For chemotaxis assays, wells were located 2 mm on either side of the target electrode along a common axis (see panel B of FIG. 2). The chambers were chilled at 4° C. for 15 minutes and then the agarose plugs were removed by aspiration using a Pasteur pipette.

The chemoattractant was then loaded into one well in appropriate chambers and the gradient was allowed to form for one hour. Cells were then loaded into the other well and the apparatus was attached to the ECIS instrumentation and the measurement of resistance was initiated. A current flow of 1 volt a.c. at 4,000 Hz was passed through the chamber at 60 second intervals. Impedance to this current flow was measured and a resistance value was calculated according to established protocols. Resistance values could be observed in real time on the computer display. In the results presented below, the data is presented as normalized resistance, which is calculated as a fraction of the initial resistance of the chamber at the start of the experiment.

Imaging

The gold electrode and overlying photoresist is thin enough to be visually transparent. For some experiments, the area of the small electrode was imaged during the collection of resistance data to establish the time of arrival of cells. The plate was placed on the stage of a Leica DM IL Microscope and images were captured every minute using a Dage CCD300 video camera and a Scion CG-7 frame grabber. Image capture was controlled and images processed using Scion Image software (Scion Inc., a derivative of NIH Image developed by Wayne Rasband at NIH). In other experiments, the chambers of a plate were periodically imaged in order to verify the data obtained by ECIS measurements.

Example 2

Measurements of Cells Responding to a Simple Chemotactic Gradient.

Figure 4:
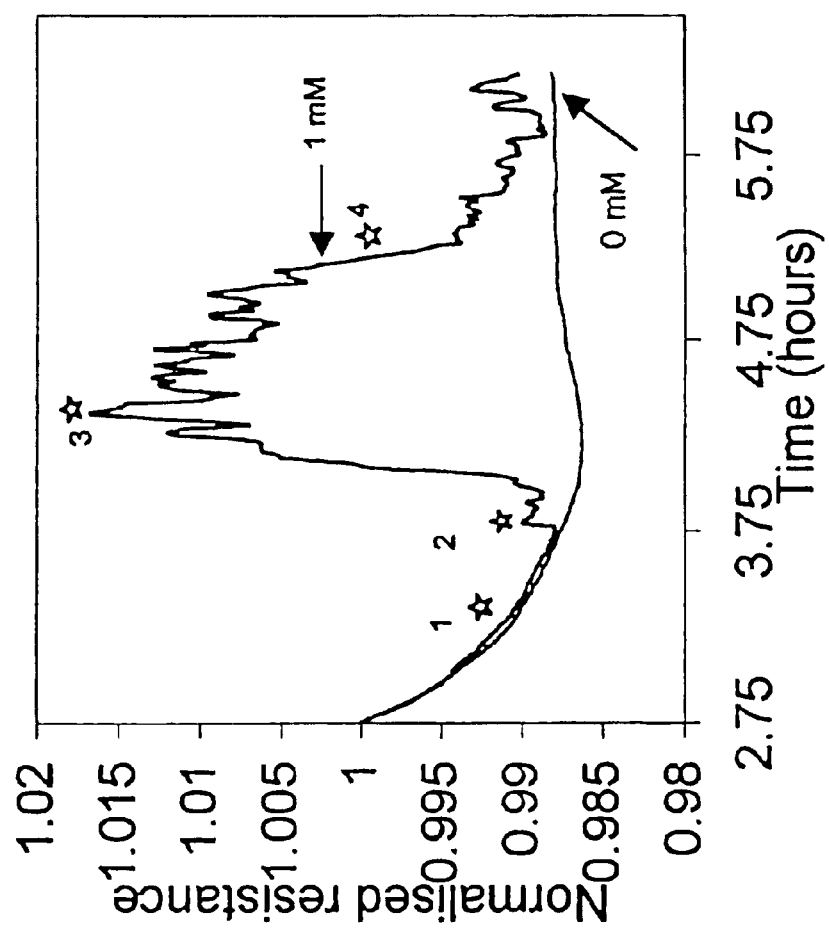
FIG. 4 is a plot of normalized resistance as a function of time illustrating the movement of *Dictyostelium discoidium* cells in response to a folic acid gradient.
Figure 5:
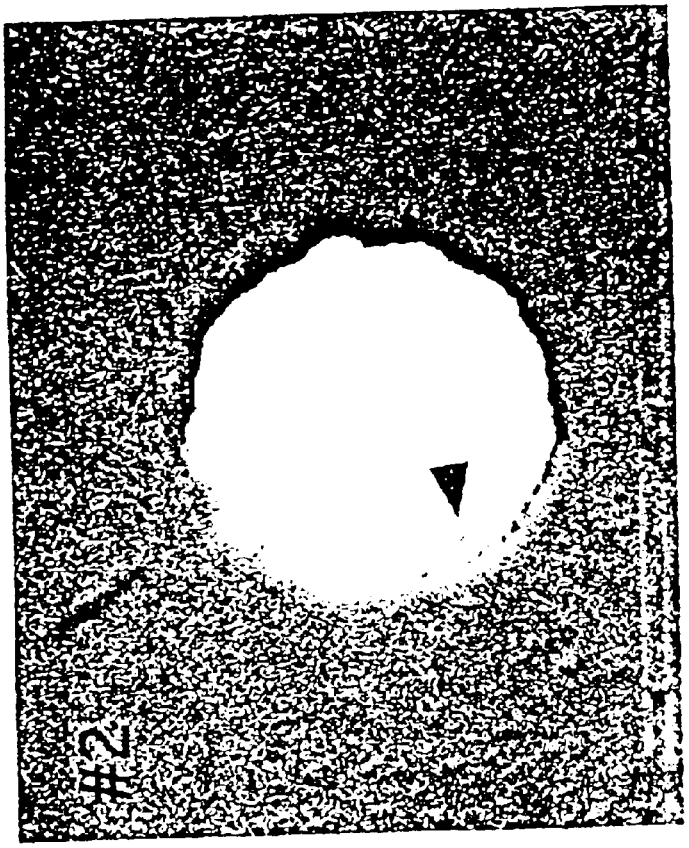
FIG. 5, in four panels, A–D, is a series of video images of the sensing electrode for which resistance data was plotted in FIG. 4 at each of the four time points specifically illustrated in FIG. 4.
Figure 5:
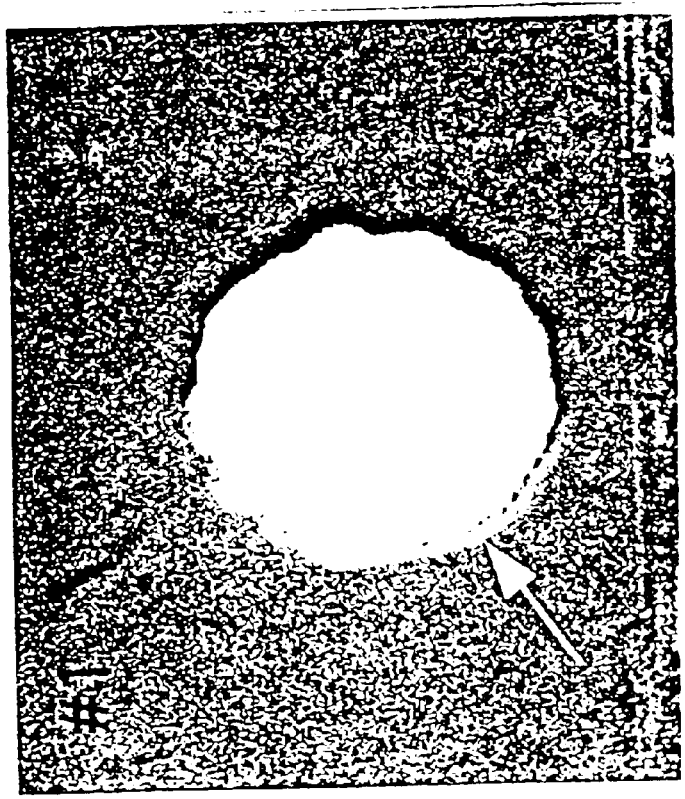
Figure 5:
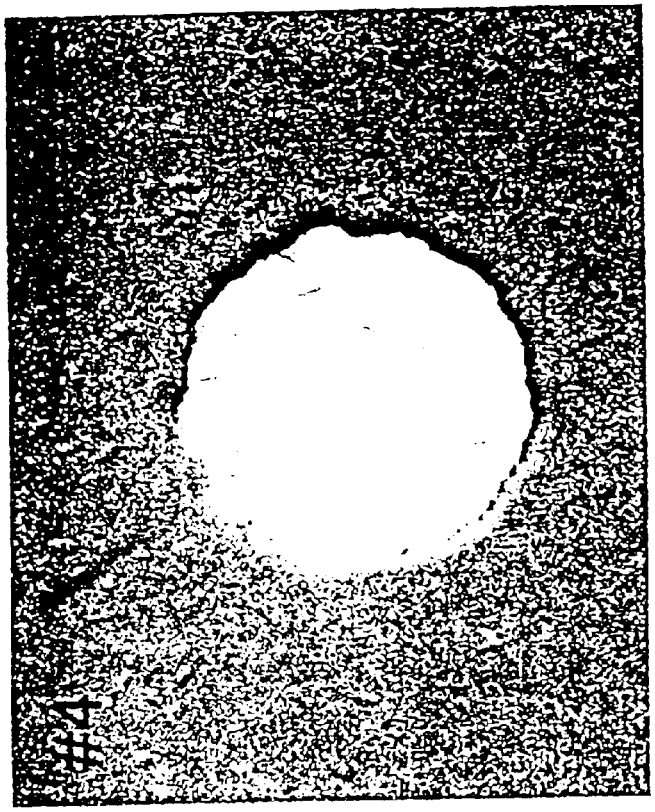
Figure 5:
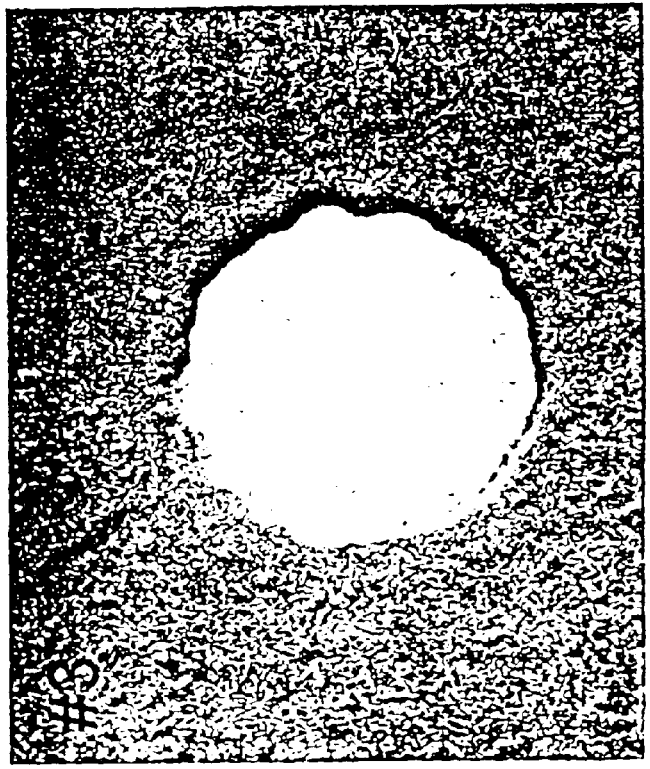
Figure 6:
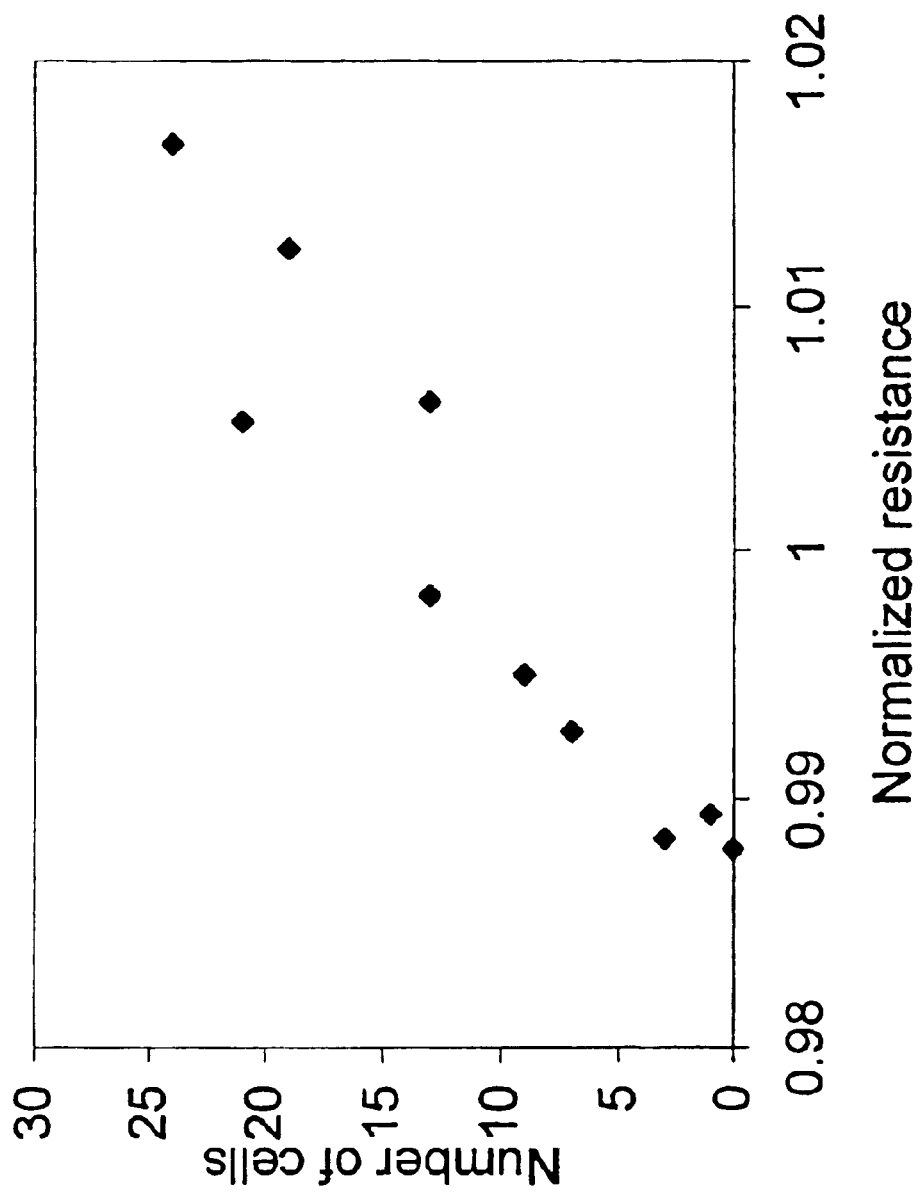
FIG. 6 is a plot of normalized resistance as a function of the number of cells detected on the surface of a sensing electrode of the cell movement assay system of the present invention.

A gradient was established by loading 1 mM folate into the chemoattractant well of a modified ECIS chamber, and one hour later Dictyostelium cells were placed in the adjacent cell well. As a control, cells were added in parallel to a well in a chamber in which no folate was added to the chemoattractant well. In order to visualize the arrival of the cells at the target electrode, the cells exposed to folate were continuously monitored by video microscopy. During the time before arrival of cells at the electrode, both the control chamber and the folate chamber show a continuous, smooth decrease in resistance (labeled *1 in FIG. 4). In the video images collected from this electrode, the leading cells can be seen approaching the target electrode from the lower left (FIG. 5, panel A). The first small peak at 3.75 hours (labeled *2 in FIG. 5, panel A) coincides with the initial cell leaving the photoresist surface and spreading on the target electrode (FIG. 5, panel B). As this first cell crawls over the electrode the resistance remains above background, and then decreases as that first cell moves off the electrode. Analysis of the time-lapse data indicates that the cell does not alter its motile behavior significantly as it changes from moving on the photoresist substrate to moving on the elemental gold electrode surface. The resistance increases again (labeled *3 in FIG. 4) as a wave of cells arrives at the electrode (FIG. 5, panel C). As the wave of cells passes, the resistance begins to gradually decrease (FIG. 5, panel D). Throughout the period of measurement, there is a correlation between the number of cells on the electrode and the measured resistance values (FIG. 6).

The average speed of cell movement to the target electrode was calculated to be approximately 10 μm/min. This speed is consistent with previous measurements of wild type Dictyostelium chemotaxis on an agar surface (6 μm/minute±1.2). In the assay system of the present invention, this movement occurs primarily on a layer of photoresist material until the cells eventually arrive at the gold target electrode surface. Cell movement is unimpeded by the 5 micron step that the cells must traverse to reach the surface of the gold electrode and must cross again as they depart the electrode at the other side (data not shown). It is interesting to note that the resistance does not change until the cell has actually contacted the electrode surface, and is unchanged as the cell remains on the edge of the photoresist/electrode interface.

The normalized resistance changes over the period before cells arrive at the surface of the target electrode in a way that appears to reflect gradual changes to the electrolyte characteristics of the culture media. This change probably reflects equilibration of the media with the external atmosphere, combined with the impact of metabolic activity of the cultured cells on the media. Since resistance is normalized to the initial reading within each chamber, this shift does not interfere with the ability to note the increase in resistance that attends the arrival of cells at the target electrode. Furthermore, the changes in resistance that attend changes to the culture conditions over time are not subject to the rapid transient changes in resistance that are characteristic of cellular activity on the electrode.

Example 3
Dictyostelium Responds to Folic Acid in a Dose Dependent Manner.

Figure 7:
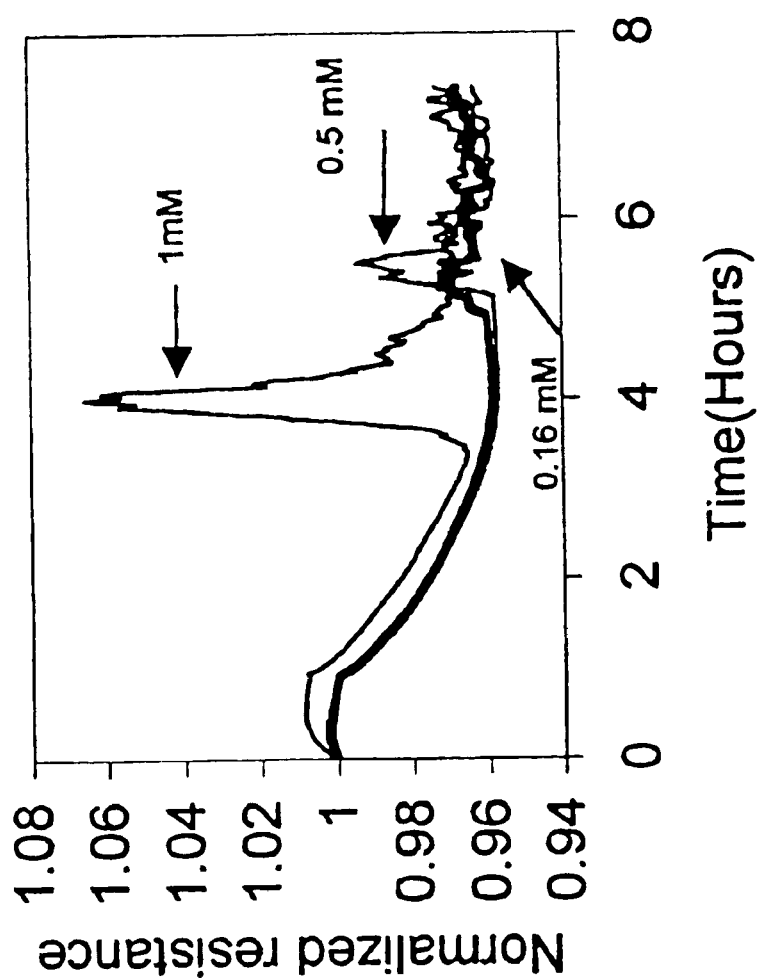
FIG. 7 is a plot of normalized resistance measured at the sensing electrode of the cell movement assay system of the present invention in a series of experiments with an increasing concentration of folic acid as the chemoattractant species.

In order to assess the sensitivity of this technique to the measurement of a range of chemotactic gradients, gradients were established by adding a range of folate concentrations (from 0.16 to 1 mM) to the chemoattractant well. Cells exposed to control media in the absence of chemoattractant did not arrive at the target electrode during the course of the experiment, hence no significant change to normalized resistance was observed (data not shown). In contrast, cells placed in the gradient formed by 1 mM folate were found to arrive at the target electrode at approximately 3.5 hours after the placement of cells in the cell well. This movement was considerably faster than the response of cells to the gradients established by either 0.5 or 0.16 mM folate. In these instances, cell arrival at the target electrode began at about 5 to 5.25 hours after addition of cells to the system. See FIG. 7.

Another notable difference that distinguishes the cells responding to each level of chemoattractant is that the absolute number of cells that arrive decreases as the dose of folate used to establish the gradient decreases. This is presumably a consequence of cells that are exposed to a suboptimal concentration of folate. One important advantage of the system of the present invention over other prior art techniques is that it allows the assessment of the whole cell population during the migratory process as opposed to looking at the fastest cells among the population. By analyzing the entire data set one can estimate the number of cells that have responded to the signal and the duration of time over which cells continue to arrive at the electrode. The observation that resistance increases in a manner proportional to the number of cells on the target electrode suggests that individual resistance values can be interpreted to reveal the size of the responding cell population. When testing new chemokines or inhibitors, this data will provide more information about the response of the population than a single time point assay.

Example 4
ECIS/taxis Measurements in a Uniform Concentration of Folate.

Another way to configure a chemotaxis assay is to add the chemoattractant uniformly throughout the agarose matrix. If the cells affect the chemoattractant (either by consuming it or by secreting enzymes that degrade it), a local gradient will form and cells will then move toward areas of higher chemoattractant concentration. For example, Dictyostelium secretes folate deaminase, which can destroy nearby folate and thereby create a folate gradient. Cells can also respond to some agents by increasing their speed of random movement (chemokinesis) which can also result in accelerated movement away from the origin.

Figure 8:
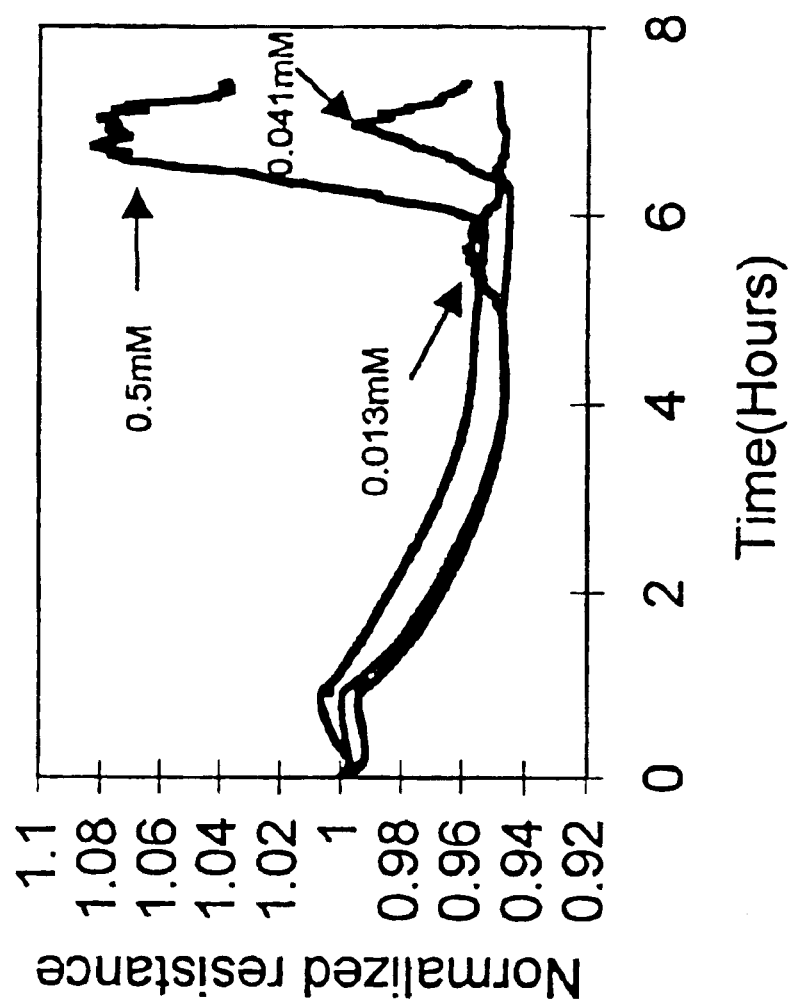
FIG. 8 is a plot of normalized resistance measured at the sensing electrode of the cell movement assay system of the present invention where cell movement was in response to a uniform concentration of chemoattractant in the gradient stabilizing medium.

In the data illustrated here, folate was mixed with the agarose before it was poured in the chamber, so that it was present at a uniform concentration throughout the chamber and surrounding the cell well. When the agarose contained 0.5 mM folate, the time of arrival of cells at the electrode was similar to arrival times for chemotactic responses to lower concentrations of folate, as illustrated in FIG. 8. Intriguingly, the cells arrive at the electrode as a wave rather than as a continuous stream even though there is a large reservoir of cells that remain in the cell well. This may result from cells altering the local concentration of folate, thus limiting the movement of cells behind the initial wave. It was interesting to note that a very low concentration of folate (0.013 mM folate) can accelerate the movement of a smaller number of Dictyostelium to a greater degree than higher concentrations. When cells are exposed to 0.013 mM folate concentration, they arrive at the target electrode approximately 1 to 1.25 hours earlier than they do when exposed to 0.04 or 0.5 mM folate.

Example 5
Identification of Cell Lines That are Unable to Produce a Chemotactic Response.

Figure 9:
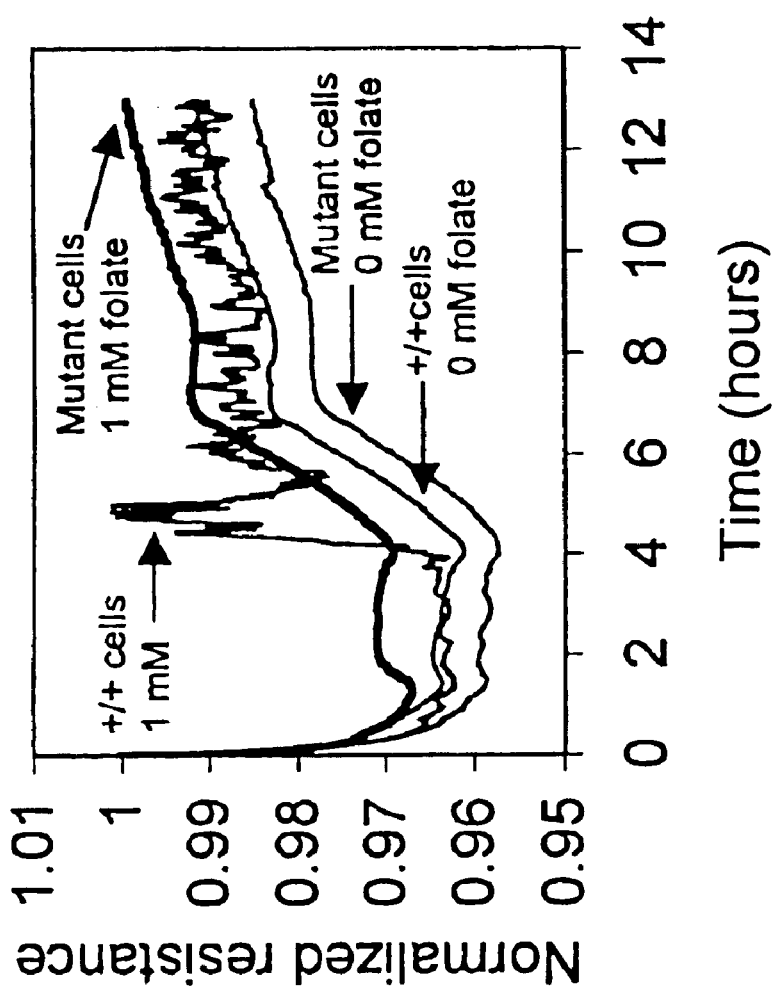
FIG. 9 is a plot of normalized resistance measured at the sensing electrode of the cell movement assay system of the present invention in a series of experiments with mutant *Dictyostelium discoidium* cells lacking the gene for the myosin II heavy chain.

An additional utility of the system of the present invention is in the identification of new mutations that contribute to the chemotactic and chemokinetic processes. In a prototypical experiment, a myosin II mutant was used that has previously been shown to have a reduced ability to respond to cyclic AMP and which is unable to move normally during morphogeneis. The response of these cells to a folate gradient has not been previously reported. The myosin II mutant cells did not arrive at the target electrode at any point during the course of the experiment (FIG. 9). Preliminary analysis has shown that at these cells do not move sufficiently far under agarose to reach the target electrode. Manipulation of the gel overlay composition may allow other aspects of cellular behavior to be examined with this technique.

Example 6
Dose-dependent Inhibition of Chemotactic Responses by Cisplatin.

Figure 10:
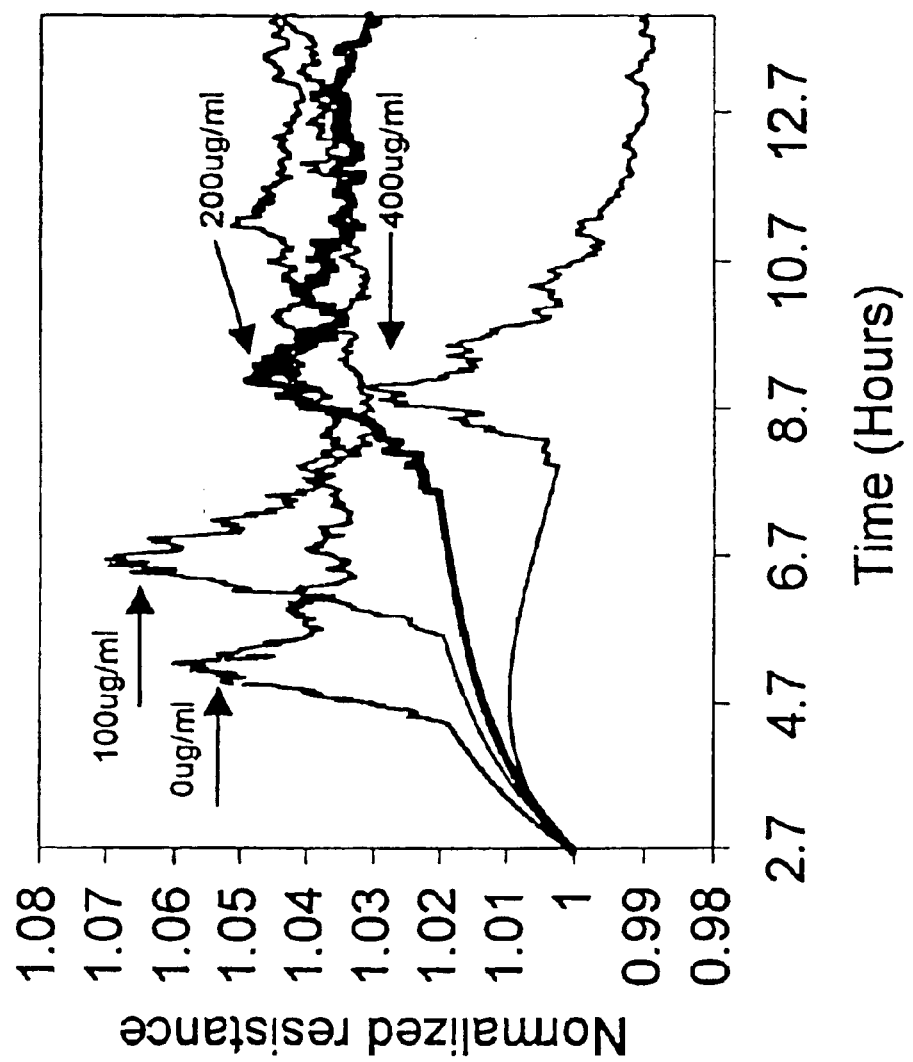
FIG. 10 is a plot of normalized resistance measured at the sensing electrode of the cell movement assay system of the present invention in a series of experiments illustrating the effect of exposure to increasing concentrations of cisplatin on the chemotactic movement of cells in response to folic acid as a chemoattractant species.

A significant potential use of the system of the present invention is in the identification of pharmacological inhibitors of chemotaxis or chemokinesis. Previous work has shown that cisplatin can decrease the chemotactic responses of Dictyostelium. When this phenomenon was examined in the system of the present invention, the time of arrival of cells at the electrode was delayed in a manner proportional to the dose of cisplatin (FIG. 10). While untreated cells reached the electrode after 4.4 hours, treated cells arrived at times that extended from 5.6 to 8 hours after the start of the experiment. The drug did not have a discernable effect on cell viability at the concentrations used, since it did not appear to affect the number of cells that eventually arrived at the electrode. Cisplatin may inhibit cell movement, through inhibition of association of actin with the cortex and/or via interactions with the signal transduction cascade. This result illustrates the potential of the system of the present invention for high throughput screening of potential agonists and antagonists of chemotactic behavior.

Figure 11:
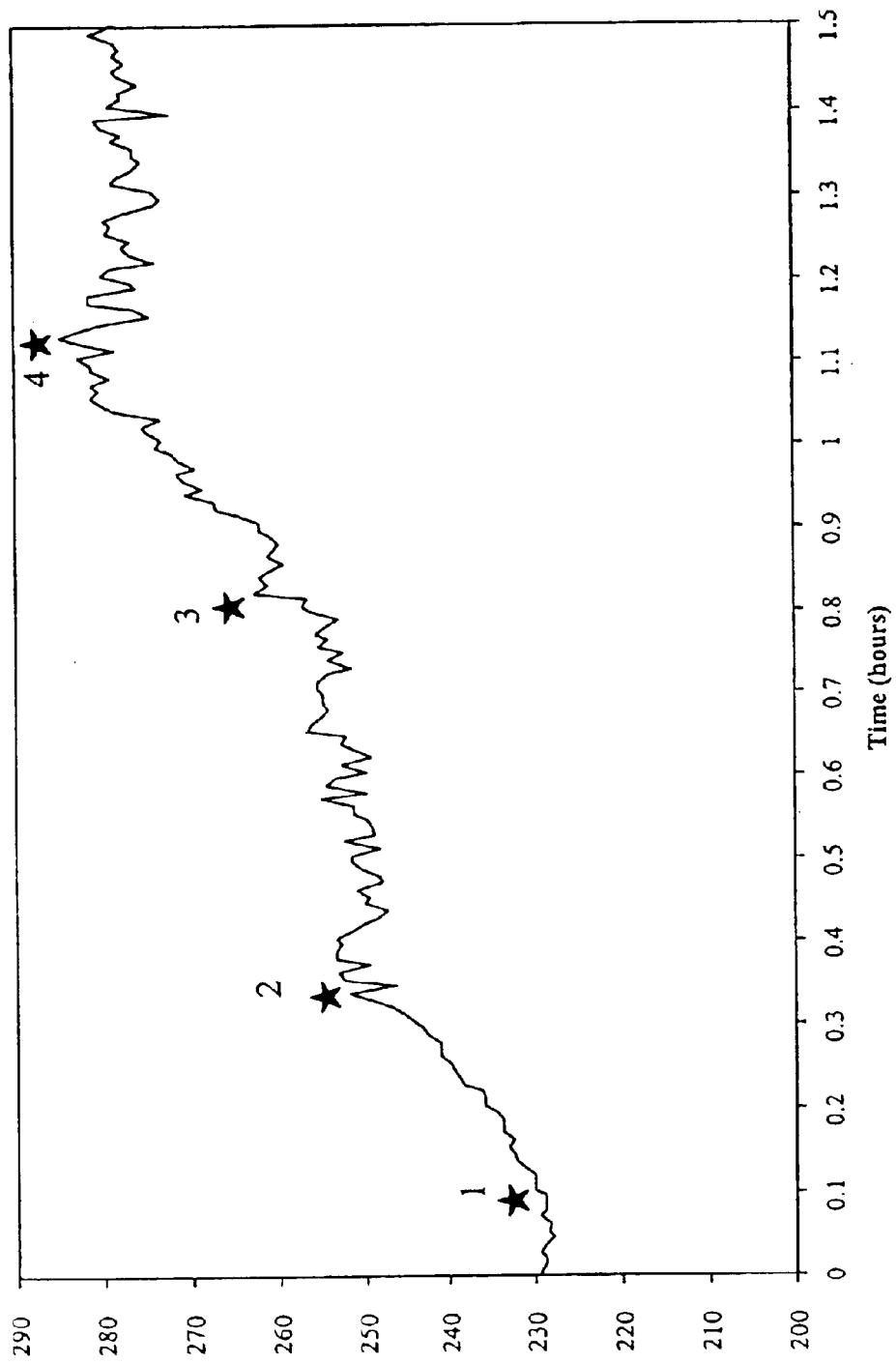
FIG. 11 is a plot of normalized resistance measured at the sensing electrode of the cell movement assay system of the present invention in a system configuration comprising a third (reference) electrode.
Figure 12:
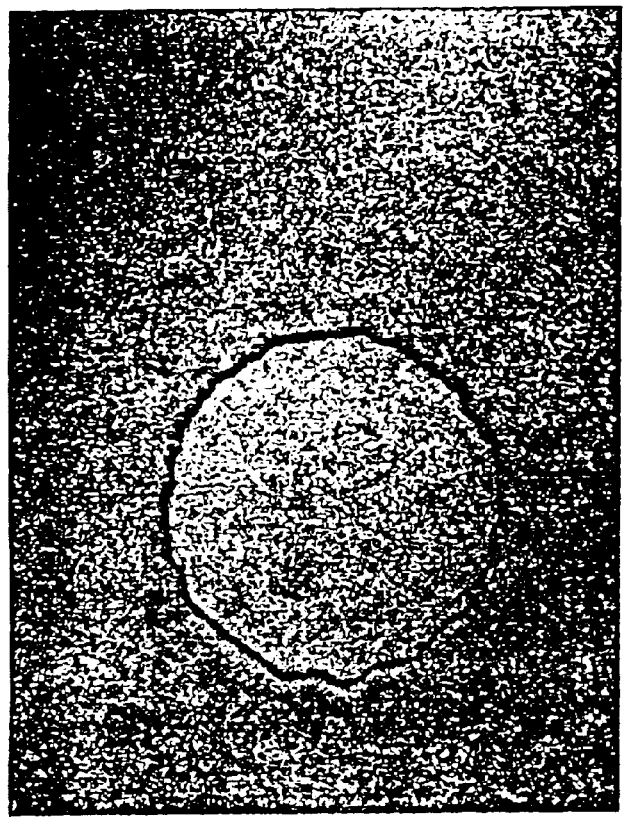
FIG. 12, in four panels, A–D, is a series of video images of the sensing electrode for which resistance data was plotted in FIG. 11 at each of the four time points specifically illustrated in FIG. 11.
Figure 12:
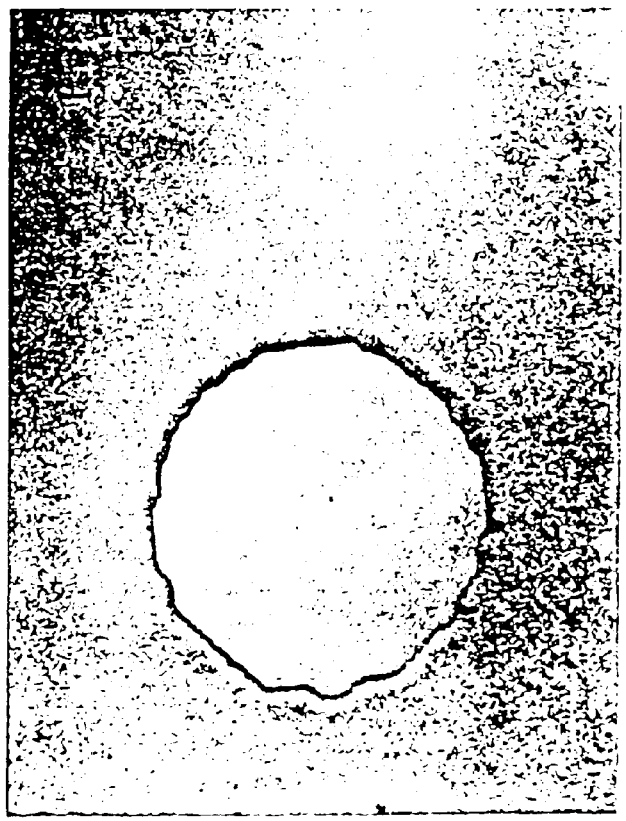
Figure 12:
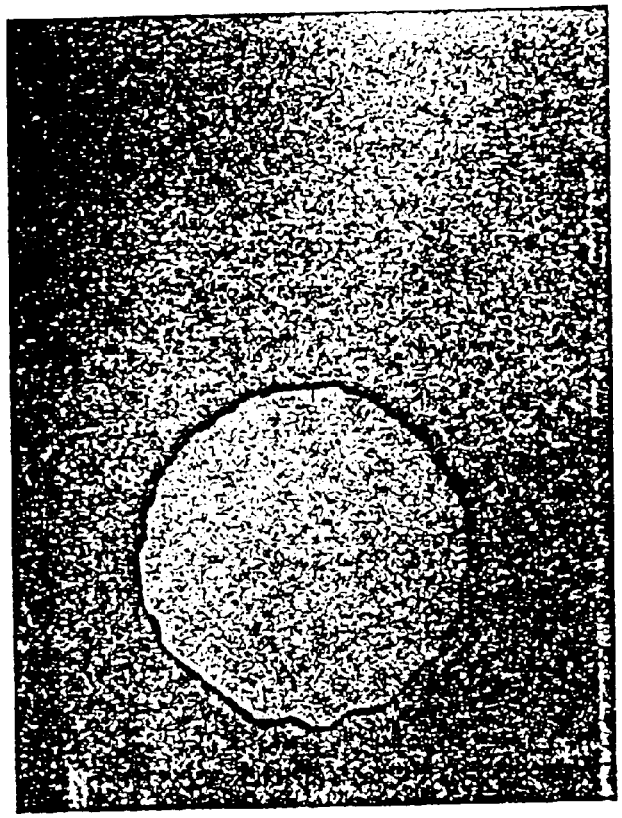
Figure 12:
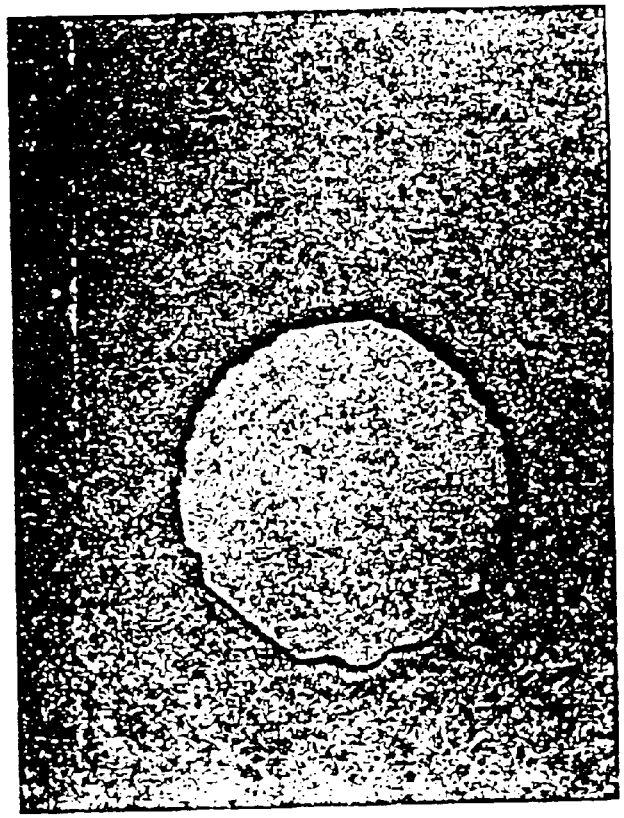

Example 7
Chemotactic Response of Bone Marrow Cells as Measured in a Three-Electrode System Bone marrow cells from BALB/c mouse were placed in the cell well of the apparatus according to procedures described above. Guinea pig serum (diluted 50:50) was simultaneously added to a chemoattractant well. The cell assay system was as described above with the addition of a reference electrode. With this three-electrode configuration, measured changes in resistance attributed to the arrival of cells at the sensing electrode can be corrected for changes in background resistance unassociated with cell interaction with the surface of the sensing electrode. Thus, measured resistance values at the sensing electrode that result from the conductive behavior of the media were subtracted from the total resistance values measured at the sensing electrode by subtracting the reference electrode readings from the sensing electrode readings at each time point. Resistance data as presented in FIG. 11 is presented from the initial time point one hour after beginning of culture. Each of the numbered points on the resistance plot of FIG. 11 represents and individual still photograph taken at that time point. The corresponding still photos are provided in FIG. 12, panels A through D.

What is claimed is:

1. A system for monitoring the effect of extracellular chemical stimuli on the translational motion of cells, the system comprising:

(a) an array of one or more cell containment wells;

(b) an array of one or more chemical attractant wells containing a chemical attractant therein interspersed among the array of one or more cell containment wells;

(c) one or more substantially planar sensing electrodes distributed within the arrays of cell containment wells and chemical attractant wells so that at least one of the sensing electrodes is between one cell containment well and one chemical attractant well, wherein the one or more sensing electrodes is operatively coupled to a sensing device capable of measuring an electrical parameter of the sensing electrode;

(d) at least one counter electrode in electrical connection with the one or more sensing electrodes; and (e) a biocompatible chemical gradient stabilizing gel medium in simultaneous diffusional contact with the arrays of cell containment wells and chemical attractant wells.

2. The system of claim 1 further comprising a reference electrode in electrical connection to the at least one counter electrode and the one or more sensing electrodes.

3. The system of claim 1, wherein the measured electrical parameter of the sensing electrode is impedance.

4. The system of claim 1, wherein the chemical gradient stabilizing gel medium is in a planar geometry overlying the arrays of cell containment wells and chemical attractant wells.

5. The system of claim 1, wherein the surface area of each of the one or more sensing electrodes is from about $0.5 \times 10^{-2}$ mm$^2$ to about $10 \times 10^{-2}$ mm$^2$.

6. The system of claim 1, wherein the sensing device is operatively coupled to a microprocessor.

7. The system of claim 6, wherein the microprocessor is under the control of a software program executable on the microprocessor.

8. A system according to claim 1 wherein said biocompatible chemical gradient stabilizing gel medium is agarose.

9. A system according to claim 1 wherein said chemical attractant is a member selected from the group consisting of folic acid, guinea pig serum, activated complement, bacterial peptides and mammalian chemokines.

10. A system according to claim 8 wherein said chemical attractant is folic acid.

* * * * *

UNITED STATES PATENT AND TRADEMARK OFFICE
CERTIFICATE OF CORRECTION

| | | |
|---|---|---|
| PATENT NO. | : 6,723,523 B2 | Page 1 of 1 |
| APPLICATION NO. | : 10/002961 | |
| DATED | : April 20, 2004 | |
| INVENTOR(S) | : Michael A. Lynes et al. | |

It is certified that error appears in the above-identified patent and that said Letters Patent is hereby corrected as shown below:

In the specification:

Insert at Col. 1, line 11 -- STATEMENT REGARDING FEDERALLY SPONSORED RESEARCH
This invention was made with government support under Grant Nos. GM040599 and AI046790 awarded by the National Institutes of Health (NIH). The government has certain rights in the invention. --

Signed and Sealed this
Thirteenth Day of September, 2011

David J. Kappos
*Director of the United States Patent and Trademark Office*